US007368273B2

(12) United States Patent
Okuda et al.

(10) Patent No.: US 7,368,273 B2
(45) Date of Patent: May 6, 2008

(54) ALKALINE PROTEASE

(75) Inventors: Mitsuyoshi Okuda, Tochigi (JP);
Tsuyoshi Sato, Tochigi (JP); Kazuhiro Saito, Tochigi (JP); Nobuyuki Sumitomo, Tochigi (JP); Yoshifumi Izawa, Tochigi (JP); Katsuhisa Saeki, Tochigi (JP); Tohru Kobayashi, Tochigi (JP); Masafumi Nomura, Wakayama (JP)

(73) Assignee: Kao Corporation, Tokyo (JP)

( * ) Notice: Subject to any disclaimer, the term of this patent is extended or adjusted under 35 U.S.C. 154(b) by 939 days.

(21) Appl. No.: 10/385,662

(22) Filed: Mar. 12, 2003

(65) Prior Publication Data

US 2004/0002432 A1 Jan. 1, 2004

(30) Foreign Application Priority Data

Mar. 22, 2002 (JP) ............................. 2002/081428
Jun. 6, 2002 (JP) ............................. 2002/165987
Oct. 18, 2002 (JP) ............................. 2002/304230
Oct. 18, 2002 (JP) ............................. 2002/304231

(51) Int. Cl.
C12N 9/48 (2006.01)
C11D 3/386 (2006.01)

(52) U.S. Cl. ..................................... 435/212; 510/300

(58) Field of Classification Search ................ 435/226
See application file for complete search history.

(56) References Cited

U.S. PATENT DOCUMENTS 5,891,701 A * 4/1999 Sloma et al. ................ 435/221
2003/0022351 A1 1/2003 Hatada, et al.

FOREIGN PATENT DOCUMENTS

EP 1 209 233 5/2002
WO WO 98/56927 12/1998
WO WO 99/18218 4/1999

OTHER PUBLICATIONS

Witkowski et al, Conversion of a beta-ketoacyl synthase to a malonyl decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
Issued_Patents_NA Database US 5,891,701 Apr. 6, 1999 Sloma et al SEQ ID No. 41. Alignment with SEQ ID No. 2.*
GenEmbl Database Accession No. AB046406 Jan. 23, 2001 from Saeki et al Biochem Biophys Res Commun. Dec. 20, 2000;279(2):313-9.*
Ito et al, Alkaline detergent enzymes from alkaliphiles. enzymatic properties, genetics, and structures. Extremophiles. Aug. 1998;2(3):185-90. Review.*
R. J. Siezen, et al., Protein Science, vol. 6, No. 3, pp. 501-523, XP-000856203, "Subtilases: The Superfamily of Subtilisin-Like Serine Proteases", Mar. 1997.
K. Saeki, et al., Database Genbank 'Online !, NCBI; Database Accession No. AB046402, 1 page, XP-002260452, "PROA Protease From *Bacillus* sp. D6", retrieved from Genbank, Jun. 16, 2001.

K. Saeki, et al., Database Genbank 'Online !, NCBI; Database Accession No. AB046404, 1 page, XP-002260453, "Proc Protease From *Bacillus* sp. Y", retrieved from Genbank, Jan. 23, 2001.
K. Saeki, et al., Database Genbank 'Online !, NCBI; Database Accession No. AB046405, 1 page, XP-002260454, "Prod Protease From *Bacillus* sp. SD521", retrieved from Genbank, Jan. 23, 2001.
K. Saeki, et al., Database Genbank 'Online !, NCBI; Database Accession No. AB046406, 1 page, XP-002260455, "Proe Protease From *Bacillus* sp. NV1", retrieved from Genbank, Jan. 23, 2001.
K. Saeki, et al., Biochemical and Biophysical Research Communications, vol. 279, pp. 313-319, "Novel Oxidatively Stable Subtilisin-Like Serine Proteases from Alkaliphilic *Bacillus* Spp.: Enzymatic Properties, Sequences, and Evolutionary Relationships", 2000.
J. A. Wells, et al., Proc. Natl. Acad. Sci., vol. 84, pp. 1219-1223, "Designing Substrate Specificity by Protein Engineering of Electrostatic Interactions", Mar. 1987.
J. A. Wells, et al., Proc. Natl. Acad. Sci., vol. 84, pp. 5167-5171, "Recruitment of Substrate-Specificity Properties From One Enzyme into a Related One by Protein Engineering", Aug. 1987.
S. Taguchi, et al., Applied and Environmental Microbiology, vol. 64, No. 2, pp. 492-495, "Engineering of a Cold-Adapted Protease by Sequential Random Mutagenesis and a Screening System", Feb. 1998.
H. Takagi, et al., Protein Engineering, vol. 11, No. 12, pp. 1205-1210, "Random Mutagenesis into the Conserved GLY 154 of Subtilisin E: Isolation and Characterization of the Reverant Enzymes", 1998.
P. N. Bryan, Biochimica et Biophysica Acta, Vol. 1543, pp. 203-222, "Protein Engineering of Subtilisin", 2000.
H. Takagi, et al., The Journal of Biological Chemistry, vol. 263, No. 36, pp. 19592-19596, "Mutant Subtilisin E With Enhanced Protease Activity Obtained by Site-Directed Mutagenesis", 1988.
U.S. Appl. No. 09/985,689, filed Nov. 5, 2001, Hatada et al.
U.S. Appl. No. 10/385,662, filed Mar. 12, 2003, Okuda et al.
U.S. Appl. No. 10/456,479, filed Jun. 9, 2003, Sato et al.

* cited by examiner

*Primary Examiner*—Sheridan Swope
(74) *Attorney, Agent, or Firm*—Oblon, Spivak, McClelland, Maier & Neustadt, P.C.

(57) ABSTRACT

An alkaline protease wherein an amino acid residue at (a) position 65, (b) position 101, (c) position 163, (d) position 17-0, (e) position 171, (f) position 273, (g) position 320, (h) position 359 or (i) position 387 of SEQ. ID NO: 2 or at a position corresponding thereto has been selected from the following amino acid residues: position (a): proline, position (b): asparagine, position (e): histidine, aspartic acid, phenylalanine, lysine, asparagine, seine, isoleucine, leucine, glutamine, threonine and valine, position (d): valine and leucine, position (e): alanine, glutamic acid, glycine and threonine, position (K): isoleucine, glycine and threonine, position (g): phenylalanine, valine, threonine, leucine, isoleucine and glycine, position (h): seine, leucine, valine, isoleucine and glutamine, position (i): alanine, lysine, glutamine, glutamic acid, arginine and histidine. A method to an alkaline protease having activity even in the presence of a highly concentrated fatty acid, and exhibiting excellent detergency for the removal of a complex stain containing protein, sebum and the like, and therefore useful as an ingredient in a detergent.

6 Claims, 1 Drawing Sheet

Fig. 1

```
KP43     1:NDVARGIVKADVAQSSYGLYGQGQIVAVADTGLDTGRNDSSMHEAFRGKITALYALGRTNNANDTNGHGTHVAGSVLGNGSTNKGMAPQA 90
KP9860   1:NDVARGIVKADVAQSSYGLYGQGQIVAVADTGLDTGRNDSSMHEAFRGKITALYALGRTNNANDTNGHGTHVAGSVLGNGATNKGMAPQA 90
KP9865   1:NDVARGIVKADVAQSSYGLYGQGQIVAVADTGLDTGRNDSSMHEAFRGKITALYALGRTNNANDTNGHGTHVAGSVLGNGSTNKGMAPQA 90
E-1      1:NDVARGIVKADVAQNNYGLYGQGQVVAVADTGLDTGRNDSSMHEAFRGKITALYALGRTNNANDPNGHGTHVAGSVLGNALNKG-MAPQA 89
Ya       1:NDVARGIVKADVAQNNYGLYGQGQVVAVADTGLDTGRNDSSMHEAFRGKITALYALGRTNNASDPNGHGTHVAGSVLGNALNKG-MAPQA 89
SD-521   1:NDVARGIVKADVAQNNYGLYGQGQVVAVADTGLDTGRNDSSMHEAFRGKITALYALGRTNNANDPNGHGTHVAGSVLGNALNKG-MAPQA 89
A-1      1:NDVARGIVKADVAQSSYGLYGQGQVVAVADTGLDTGRNDSSMHEAFRGKITAIYALGRTNNANDPNGHGTHVAGSVLGNGTSNKGMAPQA 90
A-2      1:NDVARGIVKADVAQNNFGLYGQGQIVAVADTGLDTGRNDSSMHEAFRGKITALYALGRTNNANDPNGHGTHVAGSVLGNATNK-GMAPQA 89
           ************* .******  ******************************.********.*.*************** .*****

KP43    91:NLVFQSIMDSGGGLGGLPSNLQTLFSQAYSAGARIHTNSWGAAVNGAYTTDSRNVDDYVRKNDMTILFAAGNEGPNGGTISAPGTAKNAI 180
KP9860  91:NLVFQSIMDSSGGLGGLPSNLQTLFSQAFSAGARIHTNSWGAAVNGAYTTDSRNVDDYVRKNDMTILFAAGNEGPNGGTISAPGTAKNAI 180
KP9865  91:NLVFQSIMDSGGGLGGLPSNLQTLFSQAYSAGARIHTNSWGAPVNGAYTTDSRNVDDYVRKNDMTILFAAGNEGPNGGTISAPGTAKNAI 180
E-1     90:NLVFQSIMDSSGGLGGLPSNLNTLFSQAWNAGARIHTNSWGAPVNGAYTANSRQVDEYVRNNDMTVLFAAGNEGPNSGTISAPGTAKNAI 179
Ya      90:NLVFQSIMDSSGGLGGLPSNLNTLFSQAWNAGARIHTNSWGAPVNGAYTANSRQVDEYVRNNDMTVLFAAGNEGPNSGTISAPGTAKNAI 179
SD-521  90:NLVFQSIMDSSGGLGGLPSNLNTLFSQAWNAGARIHTNSWGAPVNGAYTANSRQVDEYVRNNDMTVLFAAGNEGPNSGTISAPGTAKNAI 179
A-1     91:NLVFQSVMDSNGGLGGLPSNVSTLFSQAYSAGARIHTNSWGAPVNGAYTTDSRNVDDYVRKNDMAVLFAAGNEGPNGGTISAPGTAKNAI 180
A-2     90:NLVFQSIMDSGGGLGGLPANLQTLFSQAYSAGARIHTNSWGAPVNGAYTTDSRNVDDYVRKNDMTILFAAGNEGPGSGTISAPGTAKNAI 179
          ******.*** ******.*. ****** .************.******..**.**.***.***. ********. ***************

KP43   181:TVGATENLRPSFGSYADNINHVAQFSSRGPTKDGRIKPDVMAPGTFILSARSSLAPDSSPWANHDSKYAYMGGTSMATPIVAGNVAQLRE 270
KP9860 181:TVGATENLRPSFGSYADNINHVAQFSSRGPTKDGRIKPDVMAPGTYILSARSSLAPDSSPWANHDSKYAYMGGTSMATPIVAGNVAQLRE 270
KP9865 181:TVGATENLRPSFGSYADNINHVAQFSSRGPTKDGRIKPDVMAPGTFILSARSSLAPDSSPWANHDSKYAYMGGTSMATPIVAGNVAQLRE 270
E-1    180:TVGATENYRPSFGSIADNPNHIAQFSSRGATRDGRIKPDVTAPGTFILSARSSLAPDSSPWANYNSKYAYMGGTSMATPIVAGNVAQLRE 269
Ya     180:TVGATENYRPSFGSIADNPNHIAQFSSRGATRDGRIKPDVTAPGTPILSARSSLAPDSSPWANYNSKYAYMGGTSMATPIVAGNVAQLRE 269
SD-521 180:TVGATENYRPSFGSLADNPNHIAQFSSRGATRDGRIKPDVTAPGTFILSARSSLAPDSSPWANYNSKYAYMGGTSMATPIVAGNVAQLRE 269
A-1    181:TVGATENLRPSFGSYADNINHVAQFSSRGPTKDGRIKPDVMAPGTFILSARSSLAPDSSPWANHDSKYAYMGGTSMATPIVAGNVAQLRE 270
A-2    180:TVGATENLRPSFGSYADNINHVAQFSSRGPTRDGRIKPDVMAPGTYILSARSSLAPDSSPWANHDSKYAYMGGTSMATPIVAGNVAQLRE 269
          *******.******.***.**.*******.* ********.****.*******.******.*************.***************

KP43   271:HFVKNRGITPKPSLLKAALIAGAADIGLGYPNGNQGWGRVTLDKSLNVAYVNESSSLSTSQKATYSFTATAGKPLKISLVWSDAPASTTA 360
KP9860 271:HFVKNRGITPKPSLLKAALIAGAADIGLGYPNGNQGWGRVTLDKSLNVAYVNESSSLSTSQKATYSFTATAGKPLKISLVWSDAPASTTA 360
KP9865 271:HFVKNRGITPKPSLLKAALIAGAADIGLGYPNGNQGWGRVTLDKSLNVAYVNESSSLSTSQKATYSFTATAGKPLKISLVWSDAPASTTA 360
E-1    270:HFIKNRGITPKPSLIKAALIAGATDVGLGYPSGDQGWGRVTLDKSLNVAYVNEATALTTGQKATYSFQTQAGKPLKISLVWTDAPGSTTA 359
Ya     270:HFVKNRGITPKPSLIKAALIAGATDVGLGYPNGDQGWGRVTLNKSLNVAYVNEATALATGQKATYSFQAQAGKPLKISLVWTDAPGSTTA 359
SD-521 270:HFIKNRGITPKPSLIKAALIAGATDVGLGYPSGDQGWGRVTLDKSLNVAYVNEATALATGQKATYSFQAQAGKPLKISLVWTDAPGSTTA 359
A-1    271:HFVKNRGITPKPSLLKAALIAGATDIGLGYPSGNQGWGRVTLDKSLNVAFVNETSSLSTNQKATYSFTAQSGKPLKISLVWSDAPASTSA 360
A-2    270:HFVKNRGVTPKPSLLKAALIAGAADVGLGFPNGNQGWGRVTLDKSLNVAFVNETSPLSTSQKATYSFTAQAGKPLKISLVWSDAPGSTTA 359
          **.****.******.*.******.***.**.*.****************.*** .  *.*.*.******.*....*******.***.**.*

KP43   361:SVTLVNDLDLVITAPNGTQYVGNDPTSPYNDNWDGRNNVENVFINAPQSGTYTIEVQAYNVPVGPQTFSLAIVN    434
KP9860 361:SVTLVNDLDLVITAPNGTRYVGNDFSAPFDNNWDGRNNVENVFINSPQSGTYTIEVQAYNVPVGPQNFSLAIVN    434
KP9865 361:SVTLVNDLDLVITAPNGTQYVGNDFTSPYNDNWDGRNNVENVFINAPQSGTYTIEVQAYNVPVGPQTFSLAIVN    434
E-1    360:SYTLVNDLDLVITAPNGQKYVGNDFSYPYDNNWDGRNNVENVFINAPQSGTYTIEVQAYNVPSGPQRFSLAIVH    433
Ya     360:SYTLVNDLDLVITAPNGQKYVGNDFSYPYDNNWDGRNNVENVFINAPQSGTYIIEVQAYNVPSGPQRFSLAIVH    433
SD-521 360:SYTLVNDLDLVITAPNGQKYVGNDFSYPYDNNWDGRNNVENVFINAPQSGTYTIEVQAYNVPSGPQRFSLAIVH    433
A-1    361:SVTLVNDLDLVITAPNGTKYVGNDFTAPYDNNWDGRNNVENVFINAPQSGTYTVEVQAYNVPQGPQAFSLAIVH    434
A-2    360:SLTLVNDLDLVITAPNGTKYVGNDFTAPYDNNWDGRNNVENVFINAPQSGTYTVEVQAYNVPSPQTFSLAIVH    433
          * ***************..****** ...****************.******  *************..** ******
```

ALKALINE PROTEASE

TECHNICAL FILED

The present invention relates to an alkaline protease useful as an enzyme incorporated in a detergent, and a gene encoding the same.

BACKGROUND ART

Use of protease in industrial fields has a long history and has spread widely to various fields including detergents such as laundry detergents, fiber modifiers, leather treating agents, cosmetic compositions, bath additives, food modifiers, and pharmaceuticals. Of these, proteases for detergents are produced industrially in the largest amount. Known are, for example, Alcalase (trade mark; product of Novozymes), Savinase (trade mark; product of Novozymes), Maxacal (trade mark; product of Genencor), Blap (trade mark; product of Henkel), and KAP (product of Kao).

Proteases are incorporated into detergents for the purpose of degrading stains, which are composed mainly of proteins adhered to clothes. In practice, stains contain not only proteins but also plural components having, mixed therein, organic matters and inorganic matters such as lipids derived from sebum and solid particles. There is accordingly a demand for the development of detergents having detergency high enough to remove such a complex stain.

Finding several alkaline proteases capable of retaining caseinolytic activity even in the presence of a high concentration of fatty acids and exhibiting excellent detergency for removal of a complex stain containing both proteins and sebum, and having a molecular weight of about 43,000, the present inventors applied a patent (refer to Patent Literature 1) on them. These alkaline proteases are different in molecular weight, primary structure, enzymatic properties and markedly strong oxidant resistance from subtilisin which is a conventionally known serine protease derived from microorganisms belonging to the genus *Bacillus* so it is advocated that they should be classified into a new subtilisin sub-family (refer to Non-patent Literature 1).

The above-described alkaline proteases have caseinolytic activity even in the presence of a high concentration of fatty acids and exhibits excellent detergency for the removal of even a complex stain containing not only proteins but also sebum and the like. But its production amount is not sufficient for its production on an industrial scale. When a further improvement in detergency, as well as the production on an industrial scale, is taken into consideration, an alkaline protease having similar properties to those of the above-described alkaline proteases and having a more potent proteolytic capacity has been demanded.

Examples of the conventionally known method for enhancing secretion of a target protein (enzyme) include improvement by mutagenesis of a host strain (enzyme producing bacterium), and improvement of a gene encoding the enzyme or a gene controlling the expression of a gene encoding the enzyme. No improvement example permitting an increase in the secretion amount of subtilisin is however found.

On the other hand, for improving the proteolytic capacity, ordinarily employed is a method of altering a protease gene, thereby increasing proteolytic activity per mg of protein, that is, specific activity. There is a detailed report on protein engineering alteration for improving the specific activity of subtilisin (refer to Non-patent Literature 2, Non-patent Literature 3, Non-patent Literature 4, Non-patent Literature 5 and the like). Alterations so far reported showed an improvement in specific activity for certain synthetic peptides, but did not improve the activity toward natural substrates which is considered to have an influence on detergency.

With regards to an improvement in specific activity toward natural substrates, it is reported that proteolytic activity toward casein can be improved by replacing isoleucine at position 31 of subtilisin E with leucine (refer to Non-patent Literature 6). This case does not serve as a reference, because in the above-described alkaline protease, the corresponding amino acid is essentially leucine; and the above-described alkaline proteases are different in enzymatic properties from subtilisin having a molecular weight of about 28,000.

An object of the present invention is to provide an alkaline protease having a more potent proteolytic capacity, exhibiting excellent detergency for the removal of a complex stain, and has high secretion capacity.

Patent Literature 1: (International Publication No. 99/18218)

Non-patent Literature 1: (Saeki, et al., Biochem. Biophys. Res. Commun., 279, (2000), 313-319)

Non-patent Literature 2: (Wells, et al., Proc. Natl. Acad. Sci. USA., 84, (1987), 1219-1223)

Non-patent Literature 3: (Wells, et al., Proc. Natl. Acad. Sci. USA., 84, (1987), 5167-5171)

Non-patent Literature 4: (Taguchi, et al., Appl. Environ. Microbiol., 64, (1998), 492-495)

Non-patent Literature 5: (Takagi, et al., Protein Eng., 11, (1998), 1205-1210, Bryan, Biochim. Biophys. Acta, 1543, (2000), 203-222)

Non-patent Literature 6 (Takagi, et al., J. Biol. Chem., 36, (1988), 19592-19596)

DISCLOSURE OF THE INVENTION

The present inventors have searched a novel enzyme which can be secreted efficiently during cultivation without losing the characteristics of the above-described alkaline proteases. As a result, they have found that some alkaline proteases having a specific amino acid residue at a specific position of their amino acid sequence can meet the above-described requirements.

In one aspect of the present invention, there is thus provided an alkaline protease wherein an amino acid residue at (a) position 65, (b) position 101, (c) position 163, (d) position 170, (e) position 171, (f) position 273, (g) position 320, (h) position 359, or (i) position 387 of the amino acid sequence represented by SEQ. ID NO:1 or at a position corresponding thereto has been selected from the following amino acid residues:

position (a): a proline residue,
position (b): an asparagine residue,
position (c): a histidine, aspartic acid, phenylalanine, lysine, asparagine, serine, isoleucine, leucine, glutamine, threonine or valine residue,
position (d): a valine or leucine residue,
position (e): an alanine, glutamic acid, glycine or threonine residue,
position (f): an isoleucine, glycine or threonine residue,
position (g): a phenylalanine, valine, threonine, leucine, isoleucine or glycine residue,
position (h): a serine, leucine, valine, isoleucine, or glutamine residue, and
position (i): an alanine, lysine, glutamic acid, arginine or histidine residue.

In another aspect of the present invention, there is also provided a vector containing the gene and a transformant containing the vector.

In a further aspect of the present invention, there is also provided a detergent composition containing the alkaline protease.

BRIEF DESCRIPTION OF THE DRAWING

FIG. 1 shows amino acid sequence alignment of an alkaline protease showing at least 80% homology with the amino acid sequence of SEQ. ID NO:1.

BEST MODE FOR CARRYING OUT THE INVENTION

The alkaline protease according to the present invention has, as the amino acid residue at (a) position 65, (b) position 101, (c) position 163, (d) position 170, (e) position 171, (f) position 273, (g) position 320, (h) position 359, or (i) position 387 of the amino acid sequence of SEQ. ID NO: 2, or at a position corresponding thereto, that selected from the following amino acid residues: position (a): a proline residue, position (b): an asparagine residue, position (c): a histidine, aspartic acid, phenylalanine, lysine, asparagine, serine, isoleucine, leucine, glutamine, threonine or valine residue, position (d): a valine or leucine residue, position (e): an alanine, glutamic acid, glycine or threonine residue, position (f): an isoleucine, glycine or threonine residue, position (g): a phenylalanine, valine, threonine, leucine, isoleucine or glycine residue, position (h): a serine, leucine, valine, isoleucine or glutamine residue, and position (i): an alanine, lysine, glutamine, glutamic acid, arginine or histidine residue.

In other words, the alkaline protease of the presentinvention has an amino acid sequence represented by SEQ. ID NO: 2 wherein the amino acid residue at a position selected from the above-described (a) to (i) or at a position corresponding thereto of the amino acid sequence of another alkaline protease is a specific amino acid residue. Such an alkaline protease may be a wild type, a variant thereof, or an artificial variant.

When the alkaline protease of the present invention is a variant, those indicated as "protease having an amino acid sequence represented by SEQ. ID NO: 2" or "another alkaline protease" serve as an alkaline protease prior to mutagenesis (which may be called "parent alkaline protease"). By introducing mutation to a desired site of this parent alkaline protease, the alkaline protease of the present invention is available.

The "another alkaline protease" may be either a wild type or a wild type variant. That having oxidant resistance and having a molecular weight, as determined by sodium dodecyl sulfate polyacrylamide gel electrophoresis (SDS-PAGE), of 43,000±2,000, is preferred. Examples include alkaline proteases having an amino acid sequence showing at least 80% homology with the amino acid sequence of SEQ. ID NO: 2. Particularly preferred are those having an amino acid sequence showing at least 80%, preferably at least 87%, more preferably at least 90%, still more preferably at least 95% homology with the amino acid sequence of SEQ. ID NO: 2, working on the alkaline region of pH 8 or greater, having oxidant resistance, retains at least 80% of the original activity when treated at pH 10 for 10 minutes at 50° C., is inhibited by diisopropyl fluorophosphate (DFP) and phenylmethanesulfonyl fluoride (PMSF), and has a molecular weight, as determined by SDS-PAGE, of 43,000±2,000. The term "having oxidant resistance" as used herein means that residual activity is at least 50% of original activity when the alkaline protease is treated at 30° C. for 20 minutes in a 20 mM Britton-Robinson buffer (pH 10) containing 50 mM hydrogen peroxide and 5 mM calcium chloride.

Examples of the "alkaline protease having an amino acid sequence represented by SEQ. ID NO: 2" include KP43 [derived from *Bacillus* sp. strain KSM-KP43 (FERM BP-6532), WO99/18218], while those of the "alkaline protease having an amino acid sequence showing at least 80% homology with the amino acid sequence of SEQ. ID NO: 2" include protease KP9860 (GenBank Accession No. AB046403) [derived from *Bacillus* sp. strain KSM-KP9860 (FERM BP-6534), WO99/18218], Protease KP9865 (GenBank Accession No. AB084155) [derived from *Bacillus* sp. strain KSM-9865 (FERM P-18566), patent application Ser. No. 2002-002653], Protease E-1 (GenBank Accession No. AB046402) [derived from *Bacillus* sp. strain No. D-6 (FERM P-1592), Japanese Patent Laid-Open No. sho 49-71191], Protease Ya (GenBank Accession No. AB046404) [derived from *Bacillus* sp. strain Y (FERM BP-1029), Japanese Patent Laid-Open No. Sho 61-280268], Protease SD521 [derived from *Bacillus* sp. strain SD-521 (Genbank Accession No. AB046405) (FERM P-11162), Japanese Patent Laid-Open No. Hei 3-191781], Protease A-1 (GenBank Accession No. AB046406) [derived from NCIB12289, WO88/01293], and Protease A-2 (derived from NCIB12513, WO98/56927); a variant obtained by replacing the amino acid residue at position 46 of the amino acid sequence of SEQ. ID NO: 2 with leucine, a variant obtained by replacing the amino acid residue at position 57 with alanine, a variant obtained by replacing the amino acid residue at position 103 with arginine, a variant obtained by replacing the amino acid residue at position 107 with lysine, a variant obtained by replacing the amino acid residue at position 124 with each of lysine and alanine, a variant obtained by replacing the amino acid residue at position 136 with alanine, a variant obtained by replacing the amino acid residue at position 193 with alanine, a variant obtained by replacing the amino acid residue at position 195 with each of asparagine, glutamic acid, arginine, proline, threonine, valine, histidine, serine, lysine, glutamine, methionine, cysteine, alanine, aspartic acid, tryptophan, glycine and phenylalanine, a variant obtained by replacing the amino acid residue at position 247 with threonine and arginine, a variant obtained by replacing the amino acid at position 257 with valine, a variant obtained by replacing the amino acid residue at position 342 with alanine, and a variant obtained by replacing the amino acid residues at positions 66 and 264 with aspartic acid and serine, respectively (Japanese Patent Application No. 2000-355166); a variant obtained by replacing the amino acid residue at position 84 of SEQ. ID NO: 2 with arginine, a variant obtained by replacing the amino acid residue at position 104 with proline, a variant obtained by replacing the amino acid residue at position 256 with each of alanine and serine, and a variant obtained by replacing the amino acid residue at position 369 with asparagine (Japanese Patent Application No. 2001-114048); and a variant obtained by replacing the amino acid residue at position 251 of the amino acid sequence of SEQ. ID NO: 2 with each of asparagine, threonine, isoleucine, valine, leucine and glutamine, and a variant obtained by replacing the amino acid residue at position 256 with each of serine, glutamine, asparagine, valine and alanine (Japanese Patent Application No. 2001-329472); and alkaline proteases having at least 80%, preferably at least 87%, more preferably at least 90%, still more preferably at least 95% homology with any one of the above-described amino acid sequences.

The homology of an amino acid sequence is calculated by Lipman-Pearson's method (Science, 227, 1435(1985)). The amino acid residue of the alkaline protease represented by SEQ. ID NO: 2 is preferably threonine at position (a), glycine at position (b), glutamic acid at position (c), isoleucine at position (d), serine at position (e), valine at position (f), tyrosine at position (g), threonine at position (h), and serine at position (i). The another alkaline protease having at least 80% homology with the amino acid sequence represented by SEQ. ID NO: 2 preferably has threonine as the amino acid residue at a position corresponding to the position (a), serine as the amino acid residue at a position corresponding to the position (b), glutamic acid as the amino acid residue at a position corresponding to the position (c), isoleucine as the amino acid residue at a position corresponding to the position (d), serine as the amino acid residue at a position corresponding to the position (e), valine as the amino acid residue at a position corresponding to the position (f), tyrosine as the amino acid residue at a position corresponding to the position (g), threonine as the amino acid residue at a position corresponding to the position (h), and tyrosine as the amino acid residue at a position corresponding to the position (i).

When the alkaline protease of the present invention is a variant, preferred examples of the parent alkaline protease include, in addition to the alkaline protease having an amino acid sequence represented by SEQ. ID NO: 2 proteases having at least 80%, preferably at least 87%, more preferably at least 90%, still more preferably 95% homology with the amino acid sequence represented by the SEQ. ID NO: 2 and having the above-described enzymatic properties and/or having the above-described amino acid residues at positions corresponding to the positions (a) to (i) of SEQ. ID NO: 2.

The "amino acid residue at a position corresponding thereto" can be identified by comparing amino acid sequences by using known algorithm, for example, that of Lipman-Pearson's method, and giving maximum homology to the conserved amino acid residue existing in the amino acid sequence of each alkaline protease. The position of the corresponding amino acid residue in the sequence of each protease can be determined by aligning the amino acid sequence of the protease in such a manner irrespective of insertion or depletion in the amino acid sequence. It is presumed that the corresponding position exists at the three-dimensionally same position and it brings about similar effects for a peculiar function of the protease.

Based on FIG. 1 in which amino acid sequence is aligned by the above-described manner, (a) the amino acid residue at position 65 of SEQ. ID NO: 2 is a threonine residue. By employing the above-described method, the amino acid residue at a position corresponding thereto can be identified as the threonine residue at position 65 of, for example, Protease KP 9860. In the alkaline protease of the present invention, the amino acid residue at position 65 is preferably a proline residue.

(b) Although the amino acid residue at position 101 of SEQ. ID NO: 2 is a glycine residue, the amino acid residue of, for example, Protease E-1 at a position corresponding thereto can be identified as the serine residue at position 100 by the above-described method. In the alkaline protease of the present invention, the amino acid residue at position 101 is preferably an asparagine residue.

(c) Although the amino acid residue at position 163 of SEQ. ID NO: 2 is a glutamic acid residue, the amino acid residue of, for example, Protease E-1 at a position corresponding thereto can be identified as the glutamic acid residue at position 162 by the above-described method. In the alkaline protease of the present invention, the amino acid residue at position 163 is preferably a histidine, aspartic acid, phenylalanine, lysine, asparagine, serine, isoleucine, leucine, glutamine, threonine or valine residue, with a threonine or valine residue being particularly preferred.

(d) Although the amino acid residue at position 170 of SEQ. ID NO: 2 is an isoleucine residue, the amino acid residue of, for example, Protease E-1 at a position corresponding thereto can be identified as the isoleucine residue at position 169 by the above-described method. In the alkaline protease of the present invention, the amino acid residue at position 170 is preferably a valine or leucine residue.

(e) Although the amino acid residue at position 171 of SEQ. ID NO: 2 is a serine residue, the amino acid residue of, for example, Protease E-1 at a position corresponding thereto can be identified as the serine residue at position 170 by the above-described method. In the alkaline protease of the present invention, the amino acid residue at position 171 is preferably an alanine, glutamic acid, glycine or threonine residue, with a glycine or threonine residue being particularly preferred.

(f) Although the amino acid residue at position 273 of SEQ. ID NO: 2 is a valine residue, the amino acid residue of, for example, Protease A-2 at a position corresponding thereto can be identified as the valine residue at position 272 by the above-described method. In the alkaline protease of the present invention, the amino acid residue at position 273 is preferably an isoleucine, glycine or threonine residue, with an isoleucine residue being particularly preferred.

(g) Although the amino acid residue at position 320 of SEQ. ID NO: 2 is a tyrosine residue, an amino acid residue of, for example, Protease SD-521 at a position corresponding thereto can be identified as the tyrosine residue at position 319 by the above-described method. In the alkaline protease of the present invention, the amino acid residue at position 320 is preferably a phenylalanine, valine, threonine, leucine, isoleucine or glycine residue, with a phenylalanine residue being particularly preferred.

(h) Although the amino acid residue at position 359 of SEQ. ID NO: 2 is a threonine residue, an amino acid residue of, for example, Protease Ya at a position corresponding thereto can be identified as the threonine residue at position 358 by the above-described method. In the alkaline protease of the present invention, the amino acid residue at position 359 is preferably a serine, leucine, valine, isoleucine or glutamic acid residue, with a serine residue being particularly preferred.

(i) Although the amino acid residue at position 387 of SEQ. ID NO: 2 is a serine residue, an amino acid residue of, for example, Protease D-521 at a position corresponding thereto can be identified as the tyrosine residue at position 386 by the above-described method. In the alkaline protease of the present invention, the amino acid residue at position 387 is preferably an alanine, lysine, glutamine, glutamic acid, arginine or histidine residue, with an alanine residue being particularly preferred. Specific examples of the positions corresponding to positions (a) 65, (b) 101, (c) 163, (d) 170, (e) 171, (f) 273, (g) 320, (h) 359 and (i) 387 of the amino acid sequence (SEQ. ID NO: 2) of Protease KP43 and amino acid residues thereat are shown by preferably employed alkaline proteases among the "another alkaline protease" (Table 1).

TABLE 1

| Posi-tion | Protease | | | | | | | |
|---|---|---|---|---|---|---|---|---|
| | KP43 | KP9860 | KP9865 | E-1 | Ya | SD-521 | A-1 | A-2 |
| (a) | 65Thr | 65Thr | 65Thr | 65Pro | 65Pro | 65Pro | 65Pro | 65Pro |
| (b) | 101Gly | 101Ser | 101Gly | 100Ser | 100Ser | 100Ser | 101Asn | 100Gly |
| (c) | 163Glu | 163Glu | 163Glu | 162Glu | 162Glu | 162Glu | 163Glu | 162Glu |
| (d) | 170Ile | 170Ile | 170Ile | 169Ile | 169Ile | 169Ile | 170Ile | 169Ile |
| (e) | 171Ser | 171Ser | 171Ser | 170Ser | 170Ser | 170Ser | 171Ser | 170Ser |
| (f) | 273Val | 273Val | 273Val | 272Ile | 272Ile | 272Ile | 273Ile | 272Val |
| (g) | 320Tyr | 320Tyr | 320Tyr | 319Tyr | 319Tyr | 319Tyr | 320Phe | 319Phe |
| (h) | 359Thr | 359Thr | 359Thr | 358Thr | 358Thr | 358Thr | 359Ser | 358Thr |
| (i) | 387Ser | 387Ala | 387Ser | 386Tyr | 386Tyr | 386Tyr | 387Ala | 386Ala |

The alkaline protease of the present invention having, at position (a) 65, (b) 101, (f) 273, (g) 320, (h) 359 or (i) 387, or a position corresponding thereto, a predetermined amino acid residue has improved secretion capacity particularly when it is a transformant (refer to Example 2), while that having, at position (c) 163, (d) 170 or (e) 171, or a position corresponding thereto, a predetermined amino acid residue has particularly improved specific activity toward casein (refer to Example 3).

In the alkaline protease of the present invention, the amino acid residue may be substituted at two or more of the positions (a) to (i) simultaneously insofar as the substitution causes a change in neither enzymatic activity nor enzymatic properties. The following are preferred specific examples of the case where substitution is made at two or more positions simultaneously. The amino acid is indicated by three letters, and "+" means that substitution at one position is followed by another substitution, while "/" means that any amino acid indicated thereby is usable.

From the viewpoint of improving secretion capacity, preferred double substitution examples include Thr65Pro+Gly101Asn, Thr65Pro+Val273(Ile/Gly/Thr), Gly101Asn+Thr359 (Ser/Leu/Val/Ile/Gln), and Val273(Ile/Gly/Thr)+Tyr320(Phe/Val/Thr/Ieu/Ile/Gly), with Thr65Pro+Ser387Ala and Thr359Ser+Ser387Ala being particularly preferred. From the viewpoint of improving specific activity, preferred examples include Glu163(Phe/Leu/Gln/Val)+Ser171Ala, Glu163(Ala/Asp/Ile/Leu/Ser/Thr/Val)+Ser171Gly, and Glu163(Ala/His/Ile/Lys/Leu/Gln/Thr/Val)+Ser171Thr, with Glu163Thr+Ser171Thr, Glu163Thr+Ser171Gly and Glu163Val+Ser171Gly being particularly preferred.

From the viewpoint of improving secretion capacity, preferred triple substitution examples include Thr65Pro+Gly101Asn+Val273(Ile/Gly/Thr), Tyr320(Phe/Val/Thr/Ieu/Ile/Gly)+Val273(Ile/Gly/Thr)+Ser387(Ala/Lys/Gln/Glu/Arg/His), and Thr65Pro+Tyr320(Phe/Val/Thr/Ieu/Ile/Gly)+Thr359 (Ser/Leu/Val/Ile/Gln), with Thr65Pro+Gly101Asn+Ser387Ala, Thr65Pro+Val273Ile+Tyr320Phe and Thr65Pro+Tyr320Phe+Ser387Ala being preferred and Thr65Pro+Val273Ile+Thr359Ser, Thr65Pro+Val273Ile+Ser387Ala and Thr65Pro+Tyr320Gly+Ser387Ala being particularly preferred.

From the viewpoint of improving secretion capacity, quadruple substitution examples include Thr65Pro+Gly101Asn+Val273(Ile/Gly/Thr)+Tyr320(Phe/Val/Thr/Ieu/Ile/Gly), Thr65Pro+Tyr320(Phe/Val/Thr/Ieu/Ile/Gly)+Thr359(Ser/Leu/Val/Ile/Gln)+Ser387(Ala/Lys/Gln/Glu/Arg/His), and Gly101Asn+Val273(Ile/Gly/Thr)+Tyr320(Phe/Val/Thr/Ieu/Ile/Gly)+Ser387(Ala/Lys/Gln/Glu/Arg/His), with Thr65Pro+Val273Ile+Thr359(Ser/Leu/Ile/Val/Thr)+Ser387(Glu/Ala), Thr65Pro+Val273Ile+Tyr320(Val/Leu/Phe/Thr)+Ser387(Ala/His/Gln) being preferred; and Thr65Pro+Val273Ile+Thr359Ser+Ser387(Ala/Lys), Thr65Pro+Val273Ile+Thr359Gln+Ser387Ala, Thr65Pro+Val273Ile+Tyr320Phe+Ser387(Gln/Lys), and Thr65Pro+Val273Ile+Tyr320Ile+Ser387Gln being particularly preferred.

Quintuple or sextuple substitution can also be employed.

The alkaline protease of the present invention is available, for example, by the following method. Described specifically, it can be obtained by introducing mutation to a cloned gene encoding a parent alkaline protease (SEQ. ID No: 1), transforming a proper host by using the resulting mutated gene, culturing the resulting recombinant host, and then collecting the target alkaline protease from the cultured broth. Cloning of a gene encoding a parent alkaline protease may be carried out using ordinarily employed recombinant DNA technology, for example, in accordance with the process as described in WO99/18218 or WO98/56927.

For mutagenesis of a gene encoding a parent alkaline protease, either one of ordinarily employed random mutagenesis or site-specific mutagenesis can be adopted. More specifically, mutagenesis can be effected using, for example, "Site-Directed Mutagenesis System Mutan-Super Express Km Kit" (product of Takara Bio). A desired sequence of a gene can be replaced with a sequence of another gene corresponding to the desired sequence by using recombinant PCR (polymerase chain reaction) method (PCR protocols, Academic Press, New York, 1990).

For production of the protease of the present invention using the resulting mutated gene, usable is, for example, a method of ligating the mutated gene with a vector capable of amplifying it stably, thereby causing transformation of host bacteria, or introducing the mutated gene onto a chromosomal DNA of the host bacteria capable of maintaining the mutated gene stably. Host cells satisfying the above-described conditions include microorganisms belonging to the genus *Bacillus, Escherichia coli*, mold, yeast and the genus *Actinomyces*. Using such a strain, the host cells having the mutated gene introduced therein may be inoculated into an assimilable medium containing a carbon source, a nitrogen source and the other essential nutrients, followed by cultivation in a conventional manner.

Collection of the alkaline protease from the culture broth thus obtained, and its purification can be carried out in accordance with the ordinarily employed enzyme collection and purification methods. For example, a target enzyme is available by removing the bacteria from the cultured broth by centrifugal separation or filtration and then purifying the enzyme in a conventional manner. The enzyme solution thus obtained is usable as is, or can be purified, crystallized, pulverized or granulated further in a known manner.

The protease thus obtained has oxidant resistance, is free from the inhibition of caseinolytic activity by a high-concentration of fatty acids, has a molecular weight, as determined by SDS-PAGE, of 43,000±2,000, has activity in an alkaline region, has improved secretion capacity when it is in the form of a transformant, and/or is improved in specific activity toward casein compared with those of the parent alkaline protease.

The term "having high secretion capacity" as used herein means that when the protease activity and protein content in the supernatant are measured under similar conditions to those for the parent alkaline protease (for example, shake culture at 30° C. for 3 days after inoculation on a medium composed of 8% (w/v) polypeptone S, 0.3% yeast extract, 10% maltose, 0.04% magnesium sulfate 7 hydrate, 0.2% potassium dihydrogen phosphate, 1.5% anhydrous sodium carbonate and 30 ppm tetracycline), the alkaline protease variant showed at least predetermined enzyme activity or protein content. For example, it means that at least 5%, desirably at least 10%, more desirably at least 20% increase in the activity or protein content can be recognized. When any change in the specific activity is not recognized, either one of the activity or protein content may be measured, because the parent alkaline protease and alkaline protease variant are considered to be similar in a ratio of the activity to the protein content.

The alkaline protease variants having improved specific activity toward casein substrate compared with the parent alkaline protease have oxidant resistance, are free from the inhibition of caseinolytic activity by a high-concentration of fatty acids, have a molecular weight, as determined by SDS-PAGE, of 43,000±2,000, and have an activity in an alkaline region. Particularly preferred are those the above-described various properties of the parent alkaline protease.

Accordingly, the alkaline proteases of the present invention are useful as an enzyme to be incorporated in various detergent compositions.

Although there is no particular limitation imposed on the amount of the alkaline protease of the present invention to be added to a detergent composition insofar as it permits exhibition of its activity, it is added in an amount of from 0.1 to 5000 PU per kg of the detergent composition. In consideration of economy and the like, 500 PU or less is preferred.

To the detergent composition of the present invention, various enzymes can be used in combination with the alkaline protease of the present invention. Examples include hydrolases, oxidases, reductases, transferases, lyases, isomerases, ligases and synthetases. Of these, proteases other than the alkaline protease of the present invention, cellulases, keratinases, esterases, cutinases, amylases, lipases, pullulanases, pectinases, mannases, glucosidases, glucanases, cholesterol oxidases, peroxidases, and laccases are preferred, of which the proteases, cellulases, amylases and lipases are especially preferred. Proteases include commercially available Alcalase (trade mark; product of Novozymes), Esperase (trade mark; product of Novozymes), Savinase (trade mark; product of Novozymes), Everlase (trade mark, product of Novozymes), Kannase (trade mark, product of Novozymes), Properase (trade mark; product of Genencor International), Purafect (trade mark, product of Genencor International), and KAP (product of Kao). Cellulases include Celluzyme (trade mark; product of Novozymes), Carezyme (trade mark; product of Novozymes), KAC (product of Kao), alkaline cellulase produced by *Bacillus* sp. strain KSM-S237 as described in Japanese Patent Laid-Open No. Hei 10-313859 and mutated alkaline cellulose as described in Japanese Patent Application No. 2002-116553 (each, product of Kao). Amylases include Termamyl (trade mark; product of Novozymes), Duramyl (trade mark; product of Novozymes), Purastar (trade mark; product of Genencor International), and KAM (product of Kao). Lipases include Lipolase (trade mark; product of Novozymes) and Lipolase Ultra (trade mark, product of Novozymes).

When the protease other than the alkaline protease of the present invention is also incorporated in a detergent composition, its amount is preferably from 0.1 to 500 PU per kg of the detergent composition. When the cellulase is used in combination, it is added preferably in an amount of from 300 to 3000000 KU per kg of the detergent composition based on a unit (KU) determined by the enzymatic activity measuring method as described in [0020] of Japanese Patent Laid-Open No. Hei 10-313859. When the amylase is used in combination, it is added preferably in an amount of from 50 to 500000 IU per kg of the detergent composition based on a unit (IU) determined by the amylase activity measuring method as described in the [0040] of Japanese Patent Laid-Open No. Hei 11-43690. When the lipase is used in combination, it is added preferably in an amount of from 10000 to 1000000 LU per kg of the detergent composition based on a unit (LU) determined by the lipase activity measuring method as described in Example 1 of Japanese Language Laid-Open Publication (PCT) No. Hei 8-500013.

To the detergent composition of the present invention, known detergent components may be incorporated. Following are such known detergent components.

(1) Surfactant

A surfactant is incorporated in an amount of from 0.5 to 60 wt. % in the detergent composition. To a powdery detergent composition and a liquid detergent composition, addition of from 10 to 45 wt. % and from 20 to 50 wt. % are preferred, respectively. When the detergent composition of the present invention is a bleaching detergent or automatic dishwasher detergent, the surfactant is usually added in an amount of from 1 to 10 wt. %, preferably from 1 to 5 wt. %.

As the surfactant to be used for the detergent composition of the present invention, an anionic surfactant, a nonionic surfactant, an amphoteric surfactant and a cationic surfactant may be used either singly or in combination. Of these, the anionic surfactant and nonionic surfactant are preferred.

Examples of the nonionic surfactant include sulfate salts of a $C_{10-18}$ alcohol, sulfate salts of an alkoxylated $C_{8-20}$ alcohol, alkylbenzene sulfonate salts, paraffin sulfonate salts, α-olefin sulfonate salts, α-sulfo fatty acid salts, alkyl ester salts of an α-sulfo fatty acid, and fatty acid salts. In the present invention, linear alkylbenzene sulfonate salts having a $C_{10-14}$, more preferably $C_{12-15}$ alkyl straight chain, are particularly preferred. As the counterion, alkali metal salts and amines are preferred, of which sodium and/or potassium, monoethanolamine and diethanolamine are particularly preferred.

Preferred examples of the nonionic surfactant include polyoxyalkylene alkyl($C_{8-20}$) ethers, alkyl polyglycosides, polyoxyalkylene alkyl($C_{8-20}$) phenyl ethers, polyoxyalkylene sorbitan fatty acid ($C_{8-22}$) esters, and polyoxyalkylene glycol fatty acid ($C_{8-22}$)esters, and polyoxyethylene polyoxypropylene block copolymer. Of these, particularly preferred nonionic surfactants are polyoxyalkylene alkyl ethers [having an HLB number (as calculated by the Griffin method) of from 10.5 to 15.0, preferably from 11.0 to 14.5]

obtained by adding 4 to 20 moles of an alkylene oxide such as ethylene oxide or propylene oxide to a $C_{10-18}$ alcohol.

(2) Divalent Metal Ion Scavenger

A divalent metal ion scavenger is added in an amount of from 0.01 to 50 wt. %, preferably from 5 to 40 wt. % of the detergent composition. Examples of the divalent metal ion scavenger to be incorporated into the detergent composition of the present invention include condensed phosphates such as tripolyphosphates, pyrophosphates, and orthophosphates, aluminosilicates such as zeolites, synthetic layered crystalline silicates, nitrilotriacetates, ethylenediaminetetraacetates, citrates, isocitrates and polyacetal carboxylates. Of these, crystalline aluminosilicates (synthetic zeolites) are particularly preferred. Of zeolites type A, type X and type P, zeolite type A is particularly preferred. Synthetic zeolites having an average primary particle size of from 0.1 to 10 µm, particularly from 0.1 to 5 µm are suitably used.

(3) Alkali Agent

An alkali agent is incorporated in an amount of from 0.01 to 80 wt. %, preferably from 1 to 40 wt. % of the detergent composition. Examples of the alkali agent to be added to a powdery detergent include alkali metal carbonates such as sodium carbonate generally called dense ash or light ash, and amorphous alkali metal silicates of JIS No. 1, 2 or 3. These inorganic alkali agents are effective for forming the core of each particle upon drying a detergent and therefore, permit the preparation of a comparatively hard detergent with excellent fluidity. As well as these agents, sodium sesquicarbonate and sodium hydrogencarbonate are usable as the alkali agent. Phosphates such as tripolyphosphates also have action as an alkali agent. Examples of the alkali agents to be added to a liquid detergent include, as well as the above-described alkali agents, sodium hydroxide and mono-, di-, and tri-ethanolamines. They are usable as a counterion of the surfactant.

(4) Anti-redeposition Agent

An anti-redeposition agent is incorporated into the detergent composition in an amount of from 0.001 to 10 wt. %, preferably from 1 to 5 wt. %. Examples of anti-redeposition agent to be added to the detergent composition of the present invention include polyethylene glycol, carboxylic acid polymers, polyvinyl alcohol, and polyvinylpyrrolidone. Of these, carboxylic acid polymers have metal ion scavenging function and capacity for dispersing solid-particulate soil from clothes to a washing bath as well as anti-redeposition effect. The carboxylic acid polymers include a homopolymer or copolymers of acrylic acid, methacrylic acid, itaconic acid, or the like. As the copolymer, that obtained by copolymerizing the above-described monomer with maleic acid is preferred. The copolymer has preferably a molecular weight of several thousands to 100,000. As well as the above-described carboxylic acid polymers, polymers such as polyglycidates, cellulose derivatives such as carboxymethyl cellulose, or aminocarboxylic acid polymers such as polyaspartic acid are preferred, because they also have capacity as a metal ion scavenger and a dispersant and have anti-redeposition effect.

(5) Bleaching Agent.

A bleaching agent such as hydrogen peroxide or percarbonate is preferably added in an amount of from 1 to 10 wt. % of the detergent composition. When a bleaching agent is used, 0.01 to 10 wt. % of a bleaching activator such as tetraacetylethylenediamine (TAED) or that described in Japanese Patent Laid-Open No. Hei 6-316700 based on the amount of the detergent composition can be added.

(6) A Fluorescent Brightener

As a fluorescent brightener, biphenyl type ones (such as "Tinopal CBS-X") and stilbene type ones (such as DM fluorescent dye) can be added to the detergent composition of the present invention. It is added preferably in an amount of from 0.001 to 2% of the detergent composition.

(7) The Other Components

In the detergent composition of the present invention, a builder, softening agent, reducing agent (such as bisulfite), antifoaming agent (such as silicone), perfume and the other additives, which are known in the field of a laundry detergent, can be incorporated.

The detergent composition of the present invention can be prepared in a conventional manner by using the alkaline protease of the present invention obtained by the above-described process and the above-described known detergent components in combination. The detergent form can be selected according to the using purpose. Examples include liquid, powder, granule, paste and solid.

The detergent composition of the present invention thus available is usable as a laundry detergent, bleaching detergent, hard surface cleansing detergent, pipe cleaner, artificial tooth cleaner, sterilizing cleanser for medical tools, or the like.

EXAMPLES

Protease Activity Measuring Method—casein Method

After 1.0 mL of a 50 mM borate buffer (pH 10.5) containing 1% (w/v) of casein was kept at 30° C. for 5 minutes, 0.1 mL of an enzyme solution was added and the resulting mixture was reacted for 15 minutes. To the reaction mixture, 2.0 mL of a reaction terminating solution (0.11M trichloroacetic acid—0.22M sodium acetate—0.33M acetic acid) was added. The mixture was allowed to stand at room temperature for 30 minutes and then, filtered. The acid soluble protein in the filtrate was assayed by a modification of the method of Lowry et al. Described specifically, after addition of 2.5 mL of an alkaline copper solution [1% sodium·potassium tartrate: 1% copper sulfate 5 hydrate: 2% sodium carbonate 0.1N sodium hydroxide=1:1:100] to 0.5 mL of the filtrate, the resulting mixture was allowed to stand at room temperature for 10 minutes. Then, 0.25 mL of a phenol solution [a phenol reagent (product of Kanto Kagaku) diluted twofold with distilled water] was added. After the resulting mixture was kept at 30° C. for 30 minutes, absorbance at 660 nm was measured. One protease unit (1PU) was defined as an amount of enzyme required to liberate an acid soluble proteolytic product corresponding to 1 mmol of tyrosine for 1 min under the above-described reaction conditions.

Example 1

Random mutagenesis was introduced into an alkaline protease structural gene, which was derived from the Bacillus sp. strain KSM-KP43, of about 2.0 kb including a termination codon. For introduction of random mutagenesis, Taq polymerase: Takara Taq (product of Takara Bio) having no misincorporation recovering capacity was employed as a DNA polymerase in order to utilize misincorporation of a base in the PCR. First, PCR was conducted using Primer 1 (SEQ. ID No:3) and Primer 2 (SEQ. ID No:4) capable of amplifying this 2.0 kb DNA. Primer 1 was imparted, at the 5' end of a sense strand, with a BamHI linker, while Primer 2 was imparted, at the 5' end of the antisense strand, with an XbaI linker. As a reaction system was used a 100 μL mixture containing 10 ng of a template DNA, 10 pmol of each primer, 20 nmol of each dNTP, 10 μL of Takara Taq-added reaction buffer, and 2.5 U Taq polymerase. After denaturing of the template DNA under the PCR conditions at 94° C. for 2 minutes, PCR was performed for 30 cycles, each cycle consisting of treatment at 94° C. for 1 min, at 55° C. for 1 min and at 72° C. for 2 min. The PCR product was purified by "PCR product purification kit" (product of Roche), followed by elution in 100 μL of sterilized water. With 1 μL of the eluate as the DNA template, second PCR was conducted. The PCR product thus obtained was purified and provided for the test which will be described later.

The restriction enzyme linker of the amplified DNA fragment of about 2.0 kb was cut with BamHI and XbaI (Roche). As an expression vector to incorporate therein the amplified DNA, pHA64 (Japanese Patent Application No. Hei 8-323050; having BamHI and XbaI sites downstream of Promoter 64) replicable in bacteria belonging to *Bacillus* sp. After mixing the amplified DNA fragment treated with BamHI and XbaI, and pHA64 similarly treated with BamHI and XbaI, ligase reaction was conducted using "Ligation High" (product of Toyobo). DNA was collected from the ligase reaction mixture by ethanol precipitation and it was used as DNA for subsequent transformation.

As host cells to be transformed, *Bacillus* sp. strain KSM-KP43 (which will hereinafter be abbreviated as "strain KP-43") was employed. As the transformation method, electroporation was employed and transformation was carried out using "SSH-10" (product of Shimadzu) and Gene Pulser Cuvette (product of BioRad).

The transformant of the KP43 strain was cultured on a skim-milk-containing alkali agar medium [containing 1% skim milk (product of Difco), 1% bactotrypton (product of Difco), 0.5% yeast extract (product of Difco), 0.5% sodium chloride, 1.5% agar, 0.05% anhydrous sodium carbonate and 15 ppm tetracycline) and halo formation was observed to judge whether the protease gene was introduced or not.

The transformed strain KP43 with a plasmid having the protease gene inserted in pHA64 was selected and provided for the subsequent cultivation.

Example 2

After single colony isolation and halo formation were confirmed, the transformants obtained in Example 1 were each inoculated into a 5 mL seed medium A [6.0% (w/v) polypeptone S (product of Nippon Pharmaceutical), 0.1% yeast extract, 1.0% maltose, 0.02% magnesium sulfate 7 hydrate, 0.1% potassium dihydrogen phosphate, 0.3% anhydrous sodium carbonate and 30 ppm tetracycline] and pre-cultured overnight at 30° C. and 320 rpm. The thus—obtained seed culture medium (1% (v/v)) was inoculated into a 20 mL main culture medium [8% (w/v) polypeptone S, 0.3% yeast extract, 10% maltose, 0.04% magnesium sulfate 7 hydrate, 0.2% potassium dihydrogen phosphate, 1.5% anhydrous sodium carbonate and 30 ppm tetracycline) in a 500 mL Sakaguchi flask and cultured at 30° C. and 121 rpm for 3 days. The culture medium thus obtained was centrifuged and the protease activity in the culture supernatant was assayed. The casein method was employed for the assay of protease activity, while a Protein Assay Kit (product of Wako Pure Chemicals) was used for the assay of the protein content. The mutated protease gene whose improvement in protease activity was recognized as a result of comparison with the protease activity of the culture supernatant obtained by culturing a transformant having a wild type enzyme gene under similar conditions was selected. The protein content in the culture supernatant showed an increase in substantial proportion to the protease activity, suggesting that the mutation necessary for improving the secretion of protein content had been introduced in the variant thus obtained.

From the selected transformant, the plasmid was collected using a "High Pure Plasmid Isolation kit" (product of Roche) and the nucleotide sequence was determined. With the plasmid DNA 300 ng as a template, PCR was performed in a 20 μL reaction system by using a primer and a "Big Dye DNA Sequencing kit" (product of Applied Biosystems). The PCR product was provided for analysis using a "DNA Sequencer Model 377" (product of Applied Biosystems).

As a result, the variant having improved protease activity had threonine at position 65, glycine at position 101, valine at position 273, tyrosine at position 320, threonine at position 359 and serine at position 387 replaced with proline, asparagine, isoleucine, phenylalanine, serine and alanine, respectively. By this replacement, about 5% increase in protease activity was recognized (Table 2).

An improvement in the protease activity owing to the use of the above-described mutation sites in combination was investigated. The combination of the mutation sites was investigated using the below-descried primers and a "Site-Directed Mutagenesis System Mutan-Super Express Km kit" as means for site specific mutagenesis.

Primer 3: The threonine (T) at position 65 is replaced with proline (P) (SEQ. ID No:5)

Primer 4: The glycine (G) at position 101 is replaced with asparagine (N) (SEQ. ID No:6)

Primer 5: The valine at position 273 (V) is replaced with isoleucine (I) (SEQ. ID No:7)

Primer 6: The tyrosine at position 320 (Y) is replaced with phenylalanine (F) (SEQ. ID No:8)

Primer 7: The threonine (T) at position 359 is replaced with serine (S) (SEQ. ID No:9)

Primer 8: The serine (S) at position 387 is replaced with alanine (A) (SEQ. ID NO:10)

The template plasmid for mutation introduction was constructed by introducing the mutated protease gene, which had been obtained by the above-described screening, into the sites of BamHI and XbaI in the multi-cloning site of pKF18k having an amber mutation marker for kanamycin selection.

For PCR for introducing site-specific mutation, "Takara LA Taq" (product of Takara) was employed. PCR for mutation introduction was carried out using a 5'-end phosphorylated selection primer (a kit component of "Mutan-Super Express Km kit") and Primers 3 to 8 having mutation introduced therein, each in an amount of 5 pmol and using 10 ng of a template plasmid. After denaturing of the template DNA under reaction conditions at 94° C. for 2 minutes, PCR was performed for 30 cycles, each cycle consisting of treatment at 94° C. for 1 min, at 55° C. for 1 min and at 72° C. for 4 min. *Escherichia coli* strain MV1184 was transformed using the PCR product thus obtained, whereby a mutated plasmid was obtained. The mutated sites of the resulting mutated plasmid were confirmed in accordance with the above-described nucleotide sequence determination method.

The protease gene having mutation introduced therein by site-specific mutagenesis was introduced into pHA64 to transform the strain KP-43, followed by cultivation under the above-described conditions. The combination of the mutation sites capable of heightening the protease activity compared with that of a wild-type enzyme was studied.

As a result, a 10 to 30% improvement in the protease activity was recognized in the combination (combination of the mutation sites was indicated by+, Table 2) of T65P+ S387A, T359S+S387A, T65P+V273I+Y320F, T65P+ V273I+T359S, T65P+V273I+S387A, T65P+Y320F+ S387A, T65P+G101N+S387A, and T65P+V273U+T359S+ S387A.

The amino acid residues at positions 65, 101, 273, 320, 359 and 387 were replaced with desired amino acid residues, respectively, by using the below-described primers. An investigation was then made on whether the amino acid residue at each position was replaceable with an amino acid residue other than the above-described substituent amino acid residue or not, and a combination of the amino acid residues which were confirmed to be replaceable.

Primer 9: The threonine (T) at position 65 is replaced with a desired amino acid residue (X) (SEQ. ID NO:11)

Primer 10: The glycine (G) at position 101 is replaced with a desired amino acid residue (X) (SEQ. ID NO:12)

Primer 11: The valine (V) at position 273 is replaced with a desired amino acid residue (X) (SEQ. ID NO:13)

Primer 12: The tyrosine (Y) at position 320 is replaced with a desired amino acid residue (X) (SEQ. ID NO:14)

Primer 13: The threonine (T) at position 359 is replaced with a desired amino acid residue (X) (SEQ. ID NO:15)

Primer 14: The serine (S) at position 387 is replaced with a desired amino acid residue (X) (SEQ. ID NO:16)

As a result, an improvement in secretion of enzyme compared with that of a wild type was recognized when the valine at position 273 was replaced with, as well as isoleucine, glycine or threonine, the tyrosine at position 320 was replaced with, as well as phenylalanine, valine, threonine, leucine, isoleucine or glycine, the threonine at position 359 was replaced with, as well as serine, leucine, valine, isoleucine or glutamine and the serine at position 387 was replaced with, as well as alanine, lysine, glutamine, glutamic acid, arginine or histidine, suggesting that the amino acid replacement can be carried out at each position.

The following are the results of some combinations. A 10 to 30% improvement in the protease activity was recognized (Table 2) in the following combinations: T65P+Y320F+ S387E, T65P+Y320G+S387A, T65P+V273I+T359S+ S387E, T65P+V273I+T359L+S387A, T65P+V273I+ T359I+S387A, T65P+V273G+T359S+S387A, T65P+ V273I+T359S+S387K, T65P+V273I+T359V+S387A, T65P+V273I+T359Q+S387A, T65P+V273I+Y320F+ S387K, T65P+V273I+Y320F+S387E, T65P+V273I+ Y320F+S387K, T65P+V273T+Y320F+S387A, T65P+ V273I+Y320L+S387H, T65P+V273I+Y320V+S387Q, and T65P+V273I+Y320I+S387Q.

TABLE 2

| | Relative protease activity (%) |
|---|---|
| Wild type | 100 |
| T65P | 106 |
| G101N | 104 |
| V273I | 105 |
| Y320F | 105 |
| T359S | 106 |
| S387A | 106 |
| T65P + S387A | 107 |
| T359S + S387A | 109 |
| T65P + G101N + S387A | 114 |
| T65P + V273I + Y320F | 115 |

TABLE 2-continued

| | Relative protease activity (%) |
|---|---|
| T65P + V273I + T359S | 124 |
| T65P + V273I + S387A | 122 |
| T65P + Y320F + S387A | 123 |
| T65P + Y320F + S387E | 115 |
| T65P + V320G + S387A | 122 |
| T65P + V273I + T359S + S387A | 130 |
| T65P + V273I + T359S + S387E | 111 |
| T65P + V273I + T359L + S387A | 109 |
| T65P + V273I + T359I + S387A | 117 |
| T65P + V273G + T359S + S387A | 113 |
| T65P + V273I + T359S + S387K | 129 |
| T65P + V273I + T359V + S387A | 118 |
| T65P + V273I + T359Q + S387A | 132 |
| T65P + V273I + Y320T + S387A | 121 |
| T65P + V273I + Y320F + S387E | 128 |
| T65P + V273I + Y320F + S387K | 127 |
| T65P + V273T + Y320F + S387A | 123 |
| T65P + V273I + Y320L + S387H | 113 |
| T65P + V273I + Y320V + S387Q | 120 |
| T65P + V273I + Y320I + S387Q | 130 |

It has been confirmed that the alkaline protease available by any one of the combinations of the above-described mutation sites is improved in secretion of the enzyme when it is in the form of a transformant, while maintaining the characteristics of its parent alkaline protease, more specifically, having oxidant resistance, being free from the inhibition of caseinolytic activity by a high-concentration of fatty acids, having a molecular weight, as determined by SDS-PAGE, of 43,000±2,000, and having activity in an alkaline region.

Example 3

After single colony isolation and halo formation were confirmed, the transformants obtained in Example 1 were each inoculated into a 5 mL seed medium [6.0% (w/v) polypeptone S (product of Nippon Pharmaceutical), 0.1% yeast extract, 1.0% maltose, 0.02% magnesium sulfate 7 hydrate, 0.1% potassium dihydrogen phosphate, 0.3% anhydrous sodium carbonate and 30 ppm tetracycline] in a test tube and precultured overnight at 30° C. and 320 rpm. The seed culture medium thus obtained (1% (v/v)) was inoculated into a 20 mL main culture medium [8% (w/v) polypeptone S, 0.3% yeast extract, 10% maltose, 0.04% magnesium sulfate 7 hydrate, 0.2% potassium dihydrogen phosphate, 1.5% anhydrous sodium carbonate and 30 ppm tetracycline) in a 500 mL Sakaguchi flask and cultured at 30° C. and 121 rpm for 3 days. The culture medium thus obtained was centrifuged and the protease activity in the culture supernatant was assayed. The protease activity was assayed by the activity measuring method using casein as a substrate, while the protein content was measured using a "Protein Assay kit" (product of Wako Pure Chemicals). The mutated protease gene whose improvement in protease activity was recognized as a result of comparison with the protease activity of the culture supernatant obtained by culturing a transformant having a wild type enzyme gene under similar conditions was selected. An increase in the protein content was not so eminent relative to an increase in the protease activity in the culture supernatant, suggesting that the mutation being necessary for improving the specific activity of the enzyme was introduced in the mutated protease gene thus obtained.

From the selected transformant, the plasmid was collected using a "High Pure Plasmid Isolation kit"(product of Roche) and its base sequence was determined. With the plasmid DNA 300 ng as a template, PCR reaction was effected in a 20 µL reaction system by using a primer and a "Big Dye DNA Sequencing kit" (product of Applied Biosystem). The PCR product was provided for analysis using a "DNA Sequencer Model 377" (product of Applied Biosystem).

As a result, the variant having improved protease activity had glutamic acid at position 163, isoleucine at position 170 and serine at position 171 replaced with histidine, valine and alanine, respectively.

A portion in the culture medium was diluted, followed by application to "DEAE-Toyopearl" (product of Tosoh) equilibrated with 10 mM Tris-HCl buffer (pH 7.5) containing 2 mM calcium chloride to collect a non-adsorbed fraction, whereby a substantially uniform protease was obtained. The protein content and caseinolytic activity of the thus purified enzyme were assayed and its specific activity was calculated. As a result, it has been recognized that the above-described mutation introduction brought about an approx. 15 to 20% increase in the specific activity of protease (Table 3).

An improvement in the protease activity by replacement of the above-described mutation site with a desired amino acid was investigated. The combination of the mutation sites was investigated using the below-descried primers and a "Site-Directed Mutagenesis System Mutan-Super Express Km kit" as means for site specific mutation.

Primer 15: The glutamic acid (E) at position 163 is replaced with a desired amino acid residue (X) (SEQ. ID NO:17)

Primer 16: The isoleucine (I) at position 170 is replaced with a desired amino acid residue (X) (SEQ. ID NO:18)

Primer 17: The serine (S) at position 171 is replaced with a desired amino acid residue (X) (SEQ. ID NO:19)

Primer 18: The glutamic acid (E) at position 163 and the serine (S) at position 171 are each replaced with a desired amino acid residue (X) (SEQ. ID No:20)

The template plasmid for mutation introduction was constructed by introducing the mutated protease gene, which had been obtained by the above-described screening" into the sites of BamHI and XbaI in the multi-cloning site of pKF18k having an amber mutation marker for kanamycin selection.

For PCR reaction for introducing site-specific mutation, "Takara LA Taq" (product of Takara) was employed. Mutation introducing PCR was carried out using a 5'-end phosphorylated selection primer (a component kit of "Mutan-Super Express Km kit"), Primers 3 to 8 having mutation introduced therein, each in an amount of 5 pmol, and 10 ng of a template plasmid. After denaturalization of the template DNA under PCR reaction conditions at 94° C. for 2 minutes, PCR was performed for 30 cycles, each cycle consisting of treatment at 94° C. for 1 min, at 55° C. for 1 min and at 72° C. for 4 min. Escherichia coli strain MV1184 was transformed using the PCR product thus obtained, whereby a mutated gene was obtained. The mutated sites of the resulting mutated gene were confirmed in accordance with the above-described base sequence determination method.

The protease gene having mutation introduced therein by site-specific mutagenesis was introduced into pHA64 to transform the strain KP-43, followed by cultivation and purification under the above-described conditions. The amino acid replacement capable of heightening the specific protease activity compared with that of a wild-type enzyme was studied.

As a result, about 10 to 70% improvement in the specific activity was recognized (Table 3) in the following combinations: E163I, E163L, E163N, E163T, E163V, I170L, S171D, S171G, S171T, E163F+S171A, E163L+S171A, E163Q+S171A, E163V+S171A, E163A+S171G, E163D+S171G, E163I+S171G, E163L+S171G, E163S+S171G, E163T+S171G, E171V+S171G, E163A+S171T, E163H+S171T, E163I+S171T, E163K+S171T, E163L+S171T, E163Q+S171T, E163T+S171T, and E163V+S171T.

TABLE 3

| | Relative protease specific activity (%) |
|---|---|
| Wild type | 100 |
| E163H | 119 |
| E163I | 125 |
| E163L | 125 |
| E163N | 109 |
| E163T | 155 |
| E163V | 147 |
| I170V | 115 |
| I170L | 117 |
| S171A | 118 |
| S171D | 109 |
| S171G | 136 |
| S171T | 126 |
| E163F + S171A | 134 |
| E163L + S171A | 125 |
| E163Q + S171A | 108 |
| E163V + S171A | 131 |
| E163A + S171G | 113 |
| E163D + S171G | 119 |
| E163I + S171G | 104 |
| E163L + S171G | 106 |
| E163S + S171G | 106 |
| E163T + S171G | 156 |
| E171V + S171G | 125 |
| E163A + S171T | 119 |
| E163H + S171T | 117 |
| E163I + S171T | 131 |
| E163K + S171T | 144 |
| E163L + S171T | 144 |
| E163Q + S171T | 120 |
| E163T + S171T | 169 |
| E163V + S171T | 169 |

The alkaline protease available by any one of the above-described combinations of the mutation sites has been confirmed to have improved specific activity toward casein, while maintaining the characteristics of its parent alkaline protease, for example, having oxidant resistance, being free from the inhibition of caseinolytic activity by a high-concentration of fatty acids, having a molecular weight, as determined by SDS-PAGE, of from 43,000±2,000, and having activity in an alkali region.

Example 4

(1) Preparation of a Detergent

In a 1 m³ mixing tank equipped with a stirring blade was charged 465 kg of water. After its water temperature reached 55° C., 135 kg of a 40% (w/v) aqueous solution of sodium polyacrylate was added. The resulting mixture was stirred for 15 minutes and then, 120 kg of sodium carbonate, 60 kg of sodium sulfate, 9 kg of sodium sulfite and 3 kg of a fluorescent dye were added. After stirring for further 15 minutes, 300 kg of zeolite was added. The mixture was stirred for 30 minutes to yield a uniform slurry (the slurry had a water content of 50 wt. %). By spraying this slurry from a pressure spraying nozzle disposed in the vicinity of the top of a spray drying tower, base granules were obtained (a high temperature gas was fed to the spray drying tower at 225° C. from the bottom thereof and discharged from the top at 105° C.).

Then, 100 parts by weight of the resulting base granules were charged in a Loedige mixer (product of Matsuzaka Giken, capacity: 20L, equipped with a jacket). Under stirring by a main shaft (150 rpm), a mixture of 20 parts by weight of a nonionic surfactant, 22 parts by weight of a sodium linear-alkyl($C_{10-13}$)-benzenesulfonate, 4 parts by weight of a sodium salt of a fatty acid ($C_{14-18}$), 2 parts by weight of polyethylene glycol and 4 parts by weight of water was charged over 3 minutes, followed by stirring for 5 minutes. In the mixer charged were 20 parts by weight of crystalline sodium silicate and 10 parts by weight of zeolite to cover the surface therewith, whereby a detergent base was obtained.

The final product of the granular detergent A was obtained by mixing 99 wt. % of the detergent base with 0.5 wt. % of the protease particles of the present invention, and 0.5 wt. % of a perfume.

(2) Raw Materials Used

Nonionic surfactant: "Emulgen 108KM" (product of Kao) having, added thereto, an average of 8.5 moles of ethylene oxide Aqueous solution of sodium polyacrylate: having an average molecular weight of 10000 (prepared in accordance with the process as described in Example of Japanese Patent Publication No. Hei 2-24283)

Sodium carbonate: dense ash (product of Central Glass)

Zeolite: "Zeolite 4A" having an average particle size of 3.5 µm (product of Tosoh)

Polyethylene glycol: "K-PEG6000" (average molecular weight of 8500, product of Kao)

Crystalline sodium silicate: "SKS-6 Powder" (product of Hoechst Tokuyama)

The protease particles of the present invention: particles (6 PU/g) obtained, in accordance with the process as described in Example 1 of Japanese Patent Laid-Open No. Sho 62-257990, by granulation of each of the purified preparations of the alkaline proteases of the present invention as described in Tables 2 and 3

Fluorescent dye: "Tinopal CBS-X" (product of Ciba Geigy)

Example 5

(1) Preparation of a Detergent

A slurry having a 50 wt. % of solid content was spray dried at a hot air temperature of 250° C., whereby base granules containing 7 wt. % of sodium polyacrylate (weight average molecular weight of 10000), 26 wt. % of sodium carbonate, 20 wt. % of sodium sulfate, 6 wt. % of sodium chloride, 0.5 wt. % of a fluorescent dye, 40 wt. % of zeolite and 0.5 wt. % of water.

Then, 100 parts by weight of the resulting base granules were charged in a Loedige mixer (product of Matsuzaka Giken, capacity: 20L, equipped with a jacket). Under stirring by a main shaft (150 rpm), a mixture of 20 parts by weight of a nonionic surfactant, 22 parts by weight of a sodium linear-alkyl($C_{10-13}$)-benzenesulfonate, 4 parts by weight of a sodium salt of a fatty acid ($C_{14-18}$), 2 parts by weight of polyethylene glycol and 4 parts by weight of water was charged over 3 minutes, followed by stirring for 5 minutes. In the mixer, 20 parts by weight of crystalline sodium silicate and 10 parts by weight of zeolite were then poured to cover the surface therewith, whereby a detergent base was obtained.

The final product of the granular detergent B was obtained by mixing 95 wt. % of the detergent base with 2.8 wt. % of bleaching particles, 1.2 wt. % of bleaching activator particles, 0.5 wt. % of the protease particles of the present invention, and 0.5 wt. % of a perfume.

(2) Raw Materials Used

Nonionic surfactant: "Emulgen 108KM" (product of Kao) having, added thereto, an average of 8.5 moles of ethylene oxide Aqueous solution of sodium polyacrylate: having an average molecular weight of 10000 (prepared in accordance with the process as described in Example of Japanese Patent Publication No. Hei 2-24283)

Sodium carbonate: dense ash (product of Central Glass)

Zeolite: "Zeolite 4A" having an average particle size of 3.5 µm (product of Tosoh)

Polyethylene glycol: "K-PEG6000" (average molecular weight of 8500, product of Kao)

Crystalline sodium silicate: "SKS-6 Powder" (product of Hoechst Tokuyama)

The protease particles of the present invention: particles (6 PU/g) obtained, in accordance with the process as described in Example 1 of Japanese Patent Laid-Open No. Sho 62-257990, by granulation of each of the purified preparations of the alkaline proteases of the present invention as described in Tables 2 and 3

Fluorescent dye: "Tinopal CBS-X" (product of Ciba Geigy)

Bleaching particles: sodium carbonate·hydrogen peroxide adduct (obtained in a similar manner to that employed for the bleaching particles as described in [0019] of Japanese Patent Laid-Open No. 2000-256699)

Bleaching activator particles: granulated sodium lauroyl oxybenzenesulfonate (obtained in a similar manner to that employed for the bleaching activator particles as described in [0018] of Japanese Patent Laid-Open No. 2000-256699)

Example 6

Liquid detergent compositions (Detergent C and Detergent D) as shown in Table 4 were prepared.

TABLE 4

| Component | Detergent C (wt. %) | Detergent D (wt. %) |
|---|---|---|
| Nonionic surfactant[1] | 25.0 | — |
| Nonionic surfactant[2] | 5.0 | — |
| Nonionic surfactant[3] | 10.0 | — |
| Nonionic surfactant[4] | — | 9.0 |
| Nonionic surfactant[5] | — | 9.0 |
| Nonionic surfactant[6] | — | 2.5 |
| Anionic surfactant[7] | 1.0 | — |
| Silicone[8] | — | 0.8 |
| Carboxylic acid polymer[9] | 2.0 | — |
| Polymer[10] | — | 0.8 |
| Citric acid | 0.2 | — |
| Calcium chloride | 0.05 | — |
| Monoethanolamine | 4.0 | — |
| Triethylene glycol phenyl ether | 3.0 | — |
| Propylene glycol | 3.0 | — |
| Ethanol | 2.0 | 2.0 |
| Sodium sulfite | 0.2 | — |
| Protease of the present invention[11] | 0.5 | 1.0 |
| Perfume | 0.5 | 0.5 |

TABLE 4-continued

| Component | Detergent C (wt. %) | Detergent D (wt. %) |
|---|---|---|
| Water | Balance | Balance |
| Total | 100 | 100 |
| Concentration upon use | 20 g/30 L | 40 g/30 L |
| pH of a detergent solution | 10.5 | 7.3 |

[1])Polyoxyethylene (addition of 7 moles on average) alkyl ether having an alkyl group derived from a $C_{12-14}$ secondary alcohol ("Softanol 70", product of Nippon Shokubai)
[2])Polyoxyethylene (addition of 12 moles on average) alkyl ether having an alkyl group derived from a $C_{12-14}$ secondary alcohol ("Softanol 120", product of Nippon Shokubai)
[3])Obtained by block addition, to a $C_{10-14}$ linear primary alcohol, an average of 5 moles of EO, an average of 2 moles of PO and an average of 3 moles of EO in the order or mention.
[4])Polyoxyethylene lauryl ether having an average of 8 moles of EO added thereto.
[5])Polyoxyethylene lauryl ether having an average of 11.5 moles of EO added thereto.
[6])Narrow range polyoxyethylene alkyl (sec-$C_{12}/C_{13}$) ether
[7])Sodium $C_{10-14}$-linear alkylbenzene sulfonate
[8])Amide/ether modified silicone polymer ("BY16-906", product of Dow Corning Toray Silicone)
[9])A phenoxypolyethylene glycol-acrylic acid-maleic acid copolymer synthesized in accordance with the process as described in lines 6 to 13, page 11 of Japanese Patent Laid-Open No. Hei 10-60476 (weight average molecular weight: 10000, solid content: 51.2%)
[10])Sodium salt of a (50:50 molar ratio) copolymer of pentene and maleic acid (weight average molecular weight: 7000)
[11])Purified preparation (15 PU/g) of each alkaline protease of the present invention shown in Tables 2 and 3

Example 7

Of the components shown below in Table 5, a 40% aqueous solution of sodium polyacrylate, sodium (linear alkyl)benzenesulfonate or a nonionic surfactant, and sodium lauroyloxybenzenesulfonate were added, while stirring and mixing sodium percarbonate and sodium carbonate (dense ash). Then, the protease particles of the present invention prepared in accordance with the process as described in Example 1 of Japanese Patent Laid-Open No. Sho 62-257990 were added. The resulting mixture was stirred until the whole solution became uniform, whereby a bleaching detergent was prepared.

TABLE 5

| Component | Bleaching detergent E (wt. %) | Bleaching detergent F (wt. %) |
|---|---|---|
| Sodium percarbonate[1]) | 72.0 | 72.0 |
| Sodium carbonate (dense ash) | 20.0 | 20.0 |
| Anionic surfactant[2]) | 2.0 | — |
| Nonionic surfactant[3]) | — | 2.0 |
| Sodium polyacrylate[4]) | 1.0 | 1.0 |
| Sodium lauroyloxybenzenesulfonate | 4.0 | 4.0 |
| Protease of the present invention[5]) | 1.0 | 1.0 |

[1])Having a particle size of 500 to 700 μm
[2])A sodium salt of ($C_{12-14}$ linear alkyl)-benzenesulfonate
[3])Polyoxyethylene alkyl ether (having a $C_{12-14}$ alkyl group, an average of 12 moles of EO added)
[4])Having an average molecular weight of 8,000
[5])Granules (6 Pu/g) prepared from the purified preparation of each alkaline protease of the present invention shown in Tables 2 and 3 in accordance with the process as described in Example 1 of Japanese Patent Laid-Open No. Sho 62-257990.

Example 8

An automatic dish washing detergent compositions (Detergents G and H) shown below in Table 6 were prepared.

TABLE 6

| Component | Detergent G (wt. %) | Detergent H (wt. %) |
|---|---|---|
| Pluronic L-61[1]) | — | 4.0 |
| Softanol EP-7085[2]) | 4.0 | — |
| Trisodium citrate | — | 30.0 |
| Sodium tripolyphosphate | 30.0 | — |
| Sodium percarbonate | 20.0 | 20.0 |
| Sodium carbonate | 20.0 | 20.0 |
| Amorphous silicate[3]) | 10.0 | 10.0 |
| AA-MA[4]) | 4.0 | 4.0 |
| Sodium sulfate | 10.0 | 10.0 |
| α-amylase | 1.0 | 1.0 |
| Protease of the present invention | 1.0 | 1.0 |

[1])Polyoxyethylene-polyoxypropylene copolymer (average molecular weight: 2000)
[2])A 7-mole ethylene oxide and 8.5-mole propylene oxide adduct of a $C_{12-14}$ sec-alcohol
[3])Sodium citrate of JIS No. 2
[4])Acrylic acid-maleic acid copolymer
[5])"Duramyl 60T" ™ (product of Novozymes)
[6])Granules (6 Pu/g) obtained from the purified preparations of each alkaline protease of the present invention shown in Tables 2 and 3 in accordance with the process as described in Example 1 of Japanese Patent Laid-Open No. Sho 62-257990.

Example 9

A hard-surface detergent composition (Detergent J) was prepared using the components as shown in Table 7.

TABLE 7

| Component | Detergent J (wt. %) |
|---|---|
| Anionic surfactant[1]) | 15.0 |
| Nonionic surfactant[2]) | 5.0 |
| Nonionic surfactant[3]) | 5.0 |
| Amphoteric surfactant[4]) | 7.5 |
| Amphoteric surfactant[5]) | 4.0 |
| Citric acid | 1.0 |
| Polypropylene glycol[6]) | 2.0 |
| Ethanol | 5.0 |
| Protease of the present invention[7]) | 1.0 |
| Perfume, water, others/pH regulator | 54.5 |
| Total | 100.0 |

[1])Sodium polyoxyethylene (EOP = 4) alkyl (C12) ether sulfate
[2])Polyoxyethylene (EOP = 4) alkyl (C12) ether
[3])Alkyl (C12) polyglucoside (condensation degree: 1.3)
[4])Mono (longer chain) tertiary alkyl (C12) dimethylamine oxide
[5])Alkyl (C12) hydroxydimethylsulfobetaine
[6])Molecular weight: 10000
[7])The purified preparation (15 PU/mL) of each alkaline protease of the present invention as described in Tables 2 and 3

Example 10

The granular detergents as described below in Table 8 were obtained using the above-described detergent A (refer to Example 2).

TABLE 8

| Component (wt. %) | Detergent K | Detergent L | Detergent M | Detergent N |
|---|---|---|---|---|
| Detergent base of Example 2 | 98.4 | 98.3 | 98.5 | 97.2 |
| Perfume | 0.5 | 0.5 | 0.5 | 0.5 |
| Protease of the present invention[1]) | 0.5 | 0.5 | 0.5 | 0.5 |
| Conventional protease[2]) | | 0.6 | | 0.6 |

TABLE 8-continued

| Component (wt. %) | Detergent K | Detergent L | Detergent M | Detergent N |
|---|---|---|---|---|
| Cellulase[3] | | 0.7 | | 0.7 |
| Lipase[4] | | | 0.5 | 0.5 |

[1] Granules (6 Pu/g) prepared from the purified preparation of each alkaline protease of the present invention as described in Tables 2 and 3 in accordance with the process as described in Example 1 of Japanese Patent Laid-Open No. Sho 62-257990.
[2] Protease of 5 PU/g obtained from Protease K-16 described in Japanese Patent Laid-Open No. Hei 5-25492 in accordance with the process as described in Example 1 of Japanese Patent Laid-Open No. Sho 62-257990
[3] "KAC-500" (product of Kao)
[4] "Lipolase 100T ™" (product of Novozymes)

INDUSTRIAL APPLICABILITY

The present invention makes it possible to efficiently produce and provide an alkaline protease having activity even in the presence of a highly concentrated fatty acid, and exhibiting excellent detergency for the removal of a complex stain containing not only protein but also sebum and the like, and therefore being useful as an enzyme to be incorporated in a detergent.

We claimed:

1. An isolated polypeptide which has at least 98% homology to SEQ ID NO: 2, and which has alkaline protease activity,
   wherein the amino acid corresponding to position 65 of SEQ ID NO: 2 is proline (Pro).

2. The isolated polypeptide of claim 1, wherein said polypeptide has oxidant resistance so that at least 50% of its original activity remains after treatment at 30° C. for 20 minutes in 20 mM Britton-Robinson buffer (pH 10) containing 50 mM hydrogen peroxide and 5 mM calcium chloride.

3. The isolated polypeptide of claim 1, wherein said polypeptide has a higher specific activity toward casein compared to that of the polypeptide of SEQ ID NO: 2.

4. A detergent comprising the isolated polypeptide of claim 1.

5. The isolated polypeptide of claim 1, which comprises at least one of the following substitutions:
   the amino acid residue corresponding to position 101 of SEQ ID NO: 2 is asparagine;
   the amino acid residue corresponding to position 163 of SEQ ID NO: 2 is selected from the group consisting of histidine, aspartic acid, phenylalanine, lysine, asparagine, serine, isoleucine, leucine, glutamine, threonine and valine;
   the amino acid residue corresponding to position 170 of SEQ ID NO: 2 is valine or leucine;
   the amino acid residue corresponding to position 171 of SEQ ID NO: 2 is selected from the group consisting of alanine, glutamic acid, glycine and threonine;
   the amino acid residue corresponding to position 273 of SEQ ID NO: 2 is isoleucine, glycine or threonine;
   the amino acid residue corresponding to position 320 of SEQ ID NO: 2 is selected from the group consisting of phenylalanine, valine, threonine, leucine, isoleucine and glycine;
   the amino acid residue corresponding to position 359 of SEQ ID NO: 2 is selected from the group consisting of seine, leucine, valine, isoleucine and glutamine; or the amino acid residue corresponding to position 387 of SEQ ID NO: 2 is selected from the group consisting of alanine, lysine, glutamine, glutamic acid, arginine and histidine.

6. A detergent comprising the isolated polypeptide of claim 5.

* * * * *

SEQUENCE LISTING

<160> NUMBER OF SEQ ID NOS: 20

<210> SEQ ID NO 1
<211> LENGTH: 1305
<212> TYPE: DNA
<213> ORGANISM: Bacillus sp. KSM-KP43
<220> FEATURE:
<221> NAME/KEY: CDS
<222> LOCATION: (1)..(1305)
<223> OTHER INFORMATION:

<400> SEQUENCE: 1

```
aat gat gtt gcg cgt gga att gtc aaa gcg gat gtg gct cag agc agc      48
Asn Asp Val Ala Arg Gly Ile Val Lys Ala Asp Val Ala Gln Ser Ser
 1               5                  10                  15 tac ggg ttg tat gga caa gga cag atc gta gcg gtt gcc gat aca ggg      96
Tyr Gly Leu Tyr Gly Gln Gly Gln Ile Val Ala Val Ala Asp Thr Gly
                20                  25                  30 ctt gat aca ggt cgc aat gac agt tcg atg cat gaa gcc ttc cgc ggg     144
Leu Asp Thr Gly Arg Asn Asp Ser Ser Met His Glu Ala Phe Arg Gly
            35                  40                  45 aaa att act gca tta tat gca ttg gga cgg acg aat aat gcc aat gat     192
Lys Ile Thr Ala Leu Tyr Ala Leu Gly Arg Thr Asn Asn Ala Asn Asp
        50                  55                  60 acg aat ggt cat ggt acg cat gtg gct ggc tcc gta tta gga aac ggc     240
Thr Asn Gly His Gly Thr His Val Ala Gly Ser Val Leu Gly Asn Gly
65                  70                  75                  80 tcc act aat aaa gga atg gcg cct cag gcg aat cta gtc ttc caa tct     288
Ser Thr Asn Lys Gly Met Ala Pro Gln Ala Asn Leu Val Phe Gln Ser
                85                  90                  95 atc atg gat agc ggt ggg gga ctt gga gga cta cct tcg aat ctg caa     336
Ile Met Asp Ser Gly Gly Gly Leu Gly Gly Leu Pro Ser Asn Leu Gln
               100                 105                 110 acc tta ttc agc caa gca tac agt gct ggt gcc aga att cat aca aac     384
Thr Leu Phe Ser Gln Ala Tyr Ser Ala Gly Ala Arg Ile His Thr Asn
           115                 120                 125 tcc tgg gga gca gca gtg aat ggg gct tac aca aca gat tcc aga aat     432
Ser Trp Gly Ala Ala Val Asn Gly Ala Tyr Thr Thr Asp Ser Arg Asn
       130                 135                 140 gtg gat gac tat gtg cgc aaa aat gat atg acg atc ctt ttc gct gcc     480
Val Asp Asp Tyr Val Arg Lys Asn Asp Met Thr Ile Leu Phe Ala Ala
145                 150                 155                 160
```

```
ggg aat gaa gga ccg aac ggc gga acc atc agt gca cca ggc aca gct      528
Gly Asn Glu Gly Pro Asn Gly Gly Thr Ile Ser Ala Pro Gly Thr Ala
            165                 170                 175 aaa aat gca ata aca gtc gga gct acg gaa aac ctc cgc cca agc ttt      576
Lys Asn Ala Ile Thr Val Gly Ala Thr Glu Asn Leu Arg Pro Ser Phe
        180                 185                 190 ggg tct tat gcg gac aat atc aac cat gtg gca cag ttc tct tca cgt      624
Gly Ser Tyr Ala Asp Asn Ile Asn His Val Ala Gln Phe Ser Ser Arg
    195                 200                 205 gga ccg aca aag gat gga cgg atc aaa ccg gat gtc atg gca ccg gga      672
Gly Pro Thr Lys Asp Gly Arg Ile Lys Pro Asp Val Met Ala Pro Gly
210                 215                 220 acg ttc ata cta tca gca aga tct tct ctt gca ccg gat tcc tcc ttc      720
Thr Phe Ile Leu Ser Ala Arg Ser Ser Leu Ala Pro Asp Ser Ser Phe
225                 230                 235                 240 tgg gcg aac cat gac agt aaa tat gca tac atg ggt gga acg tcc atg      768
Trp Ala Asn His Asp Ser Lys Tyr Ala Tyr Met Gly Gly Thr Ser Met
                245                 250                 255 gct aca ccg atc gtt gct gga aac gtg gca cag ctt cgt gag cat ttt      816
Ala Thr Pro Ile Val Ala Gly Asn Val Ala Gln Leu Arg Glu His Phe
            260                 265                 270 gtg aaa aac aga ggc atc aca cca aag cct tct cta tta aaa gcg gca      864
Val Lys Asn Arg Gly Ile Thr Pro Lys Pro Ser Leu Leu Lys Ala Ala
        275                 280                 285 ctg att gcc ggt gca gct gac atc ggc ctt ggc tac ccg aac ggt aac      912
Leu Ile Ala Gly Ala Ala Asp Ile Gly Leu Gly Tyr Pro Asn Gly Asn
    290                 295                 300 caa gga tgg gga cga gtg aca ttg gat aaa tcc ctg aac gtt gcc tat      960
Gln Gly Trp Gly Arg Val Thr Leu Asp Lys Ser Leu Asn Val Ala Tyr
305                 310                 315                 320 gtg aac gag tcc agt tct cta tcc acc agc caa aaa gcg acg tac tcg     1008
Val Asn Glu Ser Ser Ser Leu Ser Thr Ser Gln Lys Ala Thr Tyr Ser
                325                 330                 335 ttt act gct act gcc ggc aag cct ttg aaa atc tcc ctg gta tgg tct     1056
Phe Thr Ala Thr Ala Gly Lys Pro Leu Lys Ile Ser Leu Val Trp Ser
            340                 345                 350 gat gcc cct gcg agc aca act gct tcc gta acg ctt gtc aat gat ctg     1104
Asp Ala Pro Ala Ser Thr Thr Ala Ser Val Thr Leu Val Asn Asp Leu
        355                 360                 365 gac ctt gtc att acc gct cca aat gga aca cag tat gta gga aat gac     1152
Asp Leu Val Ile Thr Ala Pro Asn Gly Thr Gln Tyr Val Gly Asn Asp
    370                 375                 380 ttt act tcg cca tac aat gat aac tgg gat ggc cgc aat aac gta gaa     1200
Phe Thr Ser Pro Tyr Asn Asp Asn Trp Asp Gly Arg Asn Asn Val Glu
385                 390                 395                 400 aat gta ttt att aat gca cca caa agc ggg acg tat aca att gag gta     1248
Asn Val Phe Ile Asn Ala Pro Gln Ser Gly Thr Tyr Thr Ile Glu Val
                405                 410                 415 cag gct tat aac gta ccg gtt gga cca cag acc ttc tcg ttg gca att     1296
Gln Ala Tyr Asn Val Pro Val Gly Pro Gln Thr Phe Ser Leu Ala Ile
            420                 425                 430 gtg aat taa                                                          1305
Val Asn <210> SEQ ID NO 2
<211> LENGTH: 434
<212> TYPE: PRT
<213> ORGANISM: Bacillus sp. KSM-KP43
```

<400> SEQUENCE: 2

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
    370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415
```

```
Gln Ala Tyr Asn Val Pro Val Gly Pro Gln Thr Phe Ser Leu Ala Ile
        420                 425                 430

Val Asn

<210> SEQ ID NO 3
<211> LENGTH: 47
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
aaatggatcc gtgaggaggg aaccgaatga gaaagaagaa aaaggtg                    47

<210> SEQ ID NO 4
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
atattctaga cgattaccat attaattcct ctaccc                                36

<210> SEQ ID NO 5
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
aatgccaatg atccgaatgg tcatg                                            25

<210> SEQ ID NO 6
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
tctatcatgg atagcaatgg gggacttgga gg                                    32

<210> SEQ ID NO 7
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
cttcgtgagc attttatcaa aaacagaggc atc                                   33

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
aacgttgcct ttgtgaacga gtcc                                             24
```

```
<210> SEQ ID NO 9
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
gcgagcacat ctgcttccgt aacg                                      24

<210> SEQ ID NO 10
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
tgactttact gcgccataca atgataac                                  28

<210> SEQ ID NO 11
<211> LENGTH: 36
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(18)
<223> OTHER INFORMATION: n is any one of a, g, c, or t
<220> FEATURE:
<221> NAME/KEY: misc_feature
<222> LOCATION: (19)..(19)
<223> OTHER INFORMATION: n is any one of a, g, c, or t
<220> FEATURE:
<221> NAME/KEY: misc_feature
<222> LOCATION: (20)..(20)
<223> OTHER INFORMATION: n is any one of a, g, c, or t

<400> SEQUENCE: 11
cgaataatgc caatgatnnn aatggtcatg gtacgc                         36

<210> SEQ ID NO 12
<211> LENGTH: 31
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (15)..(15)
<223> OTHER INFORMATION: n is at least one of a, g, c or t
<220> FEATURE:
<221> NAME/KEY: misc_feature
<222> LOCATION: (16)..(16)
<223> OTHER INFORMATION: n is at least one of a, g, c or t
<220> FEATURE:
<221> NAME/KEY: misc_feature
<222> LOCATION: (17)..(17)
<223> OTHER INFORMATION: n is at least one of a, g, c or t

<400> SEQUENCE: 12
ctatcatgga tagcnnnggg ggacttggag g                              31

<210> SEQ ID NO 13
<211> LENGTH: 35
<212> TYPE: DNA
<213> ORGANISM: ARTIFICIAL SEQUENCE
<220> FEATURE:
<223> OTHER INFORMATION: SYNTHETIC DNA
```

```
<220> FEATURE:
<221> NAME/KEY: misc_feature
<222> LOCATION: (13)..(13)
<223> OTHER INFORMATION: n is any one of a, g, c, or t
<220> FEATURE:
<221> NAME/KEY: misc_feature
<222> LOCATION: (14)..(14)
<223> OTHER INFORMATION: n is any one of a, g, c, or t
<220> FEATURE:
<221> NAME/KEY: misc_feature
<222> LOCATION: (15)..(15)
<223> OTHER INFORMATION: n is any one of a, g, c, or t

<400> SEQUENCE: 13
cgtgagcatt ttnnnaaaaa cagaggcatc acacc                              35

<210> SEQ ID NO 14
<211> LENGTH: 29
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (15)..(15)
<223> OTHER INFORMATION: n is at least one of a, g, c, or t
<220> FEATURE:
<221> NAME/KEY: misc_feature
<222> LOCATION: (16)..(16)
<223> OTHER INFORMATION: n is at least one of a, g, c, or t
<220> FEATURE:
<221> NAME/KEY: misc_feature
<222> LOCATION: (17)..(17)
<223> OTHER INFORMATION: n is at least one of a, g, c, or t

<400> SEQUENCE: 14
ccctgaacgt tgccnnngtg aacgagtcc                                     29

<210> SEQ ID NO 15
<211> LENGTH: 30
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (15)..(15)
<223> OTHER INFORMATION: n is at least one of a, g, c, or t
<220> FEATURE:
<221> NAME/KEY: misc_feature
<222> LOCATION: (16)..(16)
<223> OTHER INFORMATION: n is at least one of a, g, c, or t
<220> FEATURE:
<221> NAME/KEY: misc_feature
<222> LOCATION: (17)..(17)
<223> OTHER INFORMATION: n is at least one of a, g, c, or t

<400> SEQUENCE: 15
cccctgcgag cacannngct tccgtaacgc                                    30

<210> SEQ ID NO 16
<211> LENGTH: 36
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (16)..(16)
<223> OTHER INFORMATION: n is at least one of a, g, c, or t
```

<220> FEATURE:
<221> NAME/KEY: misc_feature
<222> LOCATION: (17)..(17)
<223> OTHER INFORMATION: n is at least one of a, g, c, or t
<220> FEATURE:
<221> NAME/KEY: misc_feature
<222> LOCATION: (18)..(18)
<223> OTHER INFORMATION: n is at least one of a, g, c, or t

<400> SEQUENCE: 16
ggaaatgact ttactnnncc atacaatgat aactgg                36

<210> SEQ ID NO 17
<211> LENGTH: 28
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (14)..(14)
<223> OTHER INFORMATION: n is at least one of a, g, c, or t
<220> FEATURE:
<221> NAME/KEY: misc_feature
<222> LOCATION: (15)..(15)
<223> OTHER INFORMATION: n is at least one of a, g, c, or t
<220> FEATURE:
<221> NAME/KEY: misc_feature
<222> LOCATION: (16)..(16)
<223> OTHER INFORMATION: n is at least one of a, g, c, or t

<400> SEQUENCE: 17
cgctgccggg aatnnnggac cgaacggc                28

<210> SEQ ID NO 18
<211> LENGTH: 33
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (16)..(16)
<223> OTHER INFORMATION: n is at least one of a, g, c, or t
<220> FEATURE:
<221> NAME/KEY: misc_feature
<222> LOCATION: (17)..(17)
<223> OTHER INFORMATION: n is at least one of a, g, c, or t
<220> FEATURE:
<221> NAME/KEY: misc_feature
<222> LOCATION: (18)..(18)
<223> OTHER INFORMATION: n is at least one of a, g, c, or t

<400> SEQUENCE: 18
ccgaacggcg gaaccnnnag tgcaccaggc aca                33

<210> SEQ ID NO 19
<211> LENGTH: 30
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (14)..(14)
<223> OTHER INFORMATION: n is at least one of a, g, c, or t
<220> FEATURE:
<221> NAME/KEY: misc_feature
<222> LOCATION: (15)..(15)
<223> OTHER INFORMATION: n is at least one of a, g, c, or t

```
<220> FEATURE:
<221> NAME/KEY: misc_feature
<222> LOCATION: (16)..(16)
<223> OTHER INFORMATION: n is at least one of a, g, c, or t

<400> SEQUENCE: 19
cggcggaacc atcnnngcac caggcacagc                                     30

<210> SEQ ID NO 20
<211> LENGTH: 54
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (14)..(14)
<223> OTHER INFORMATION: n is at least one of a, g, c, or t
<220> FEATURE:
<221> NAME/KEY: misc_feature
<222> LOCATION: (15)..(15)
<223> OTHER INFORMATION: n is at least one of a, g, c, or t
<220> FEATURE:
<221> NAME/KEY: misc_feature
<222> LOCATION: (16)..(16)
<223> OTHER INFORMATION: n is at least one of a, g, c, or t
<220> FEATURE:
<221> NAME/KEY: misc_feature
<222> LOCATION: (38)..(38)
<223> OTHER INFORMATION: n is at least one of a, g, c, or t
<220> FEATURE:
<221> NAME/KEY: misc_feature
<222> LOCATION: (39)..(39)
<223> OTHER INFORMATION: n is at least one of a, g, c, or t
<220> FEATURE:
<221> NAME/KEY: misc_feature
<222> LOCATION: (40)..(40)
<223> OTHER INFORMATION: n is at least one of a, g, c, or t

<400> SEQUENCE: 20
cgctgccggg aatnnnggac cgaacggcgg aaccatcnnn gcaccaggca cagc           54
```